US008930178B2

(12) United States Patent  
Pestian et al.

(10) Patent No.: US 8,930,178 B2  
(45) Date of Patent: Jan. 6, 2015

(54) PROCESSING TEXT WITH DOMAIN-SPECIFIC SPREADING ACTIVATION METHODS

(75) Inventors: John Pestian, Loveland, OH (US); Pawel Matykiewicz, Cincinnati, OH (US); Wlodzislaw Duch, Torun (PL); Tracy Glauser, Cincinnati, OH (US); Robert A. Kowatch, Cincinnati, OH (US); Jacqueline Grupp-Phelan, Terrace Park, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 1556 days.

(21) Appl. No.: 12/006,813

(22) Filed: Jan. 4, 2008

(65) Prior Publication Data

US 2008/0270120 A1    Oct. 30, 2008

Related U.S. Application Data

(60) Provisional application No. 60/878,718, filed on Jan. 4, 2007.

(51) Int. Cl.
| | | |
|---|---|---|
| *G06F 17/27* | (2006.01) | |
| *G06F 17/20* | (2006.01) | |
| *G06F 17/21* | (2006.01) | |
| *G06Q 50/22* | (2012.01) | |

(52) U.S. Cl.
CPC ............ *G06F 17/2785* (2013.01); *G06Q 50/22* (2013.01)
USPC ..................................... 704/9; 704/1; 704/10

(58) Field of Classification Search
CPC .......... G06F 19/3487; G06F 17/30616; G06F 17/2785; G06F 19/345; G06F 17/30734
USPC ....................................... 704/1, 9
See application file for complete search history.

(56) References Cited

U.S. PATENT DOCUMENTS

| | | | | |
|---|---|---|---|---|
| 6,006,221 | A * | 12/1999 | Liddy et al. ........................... | 1/1 |
| 6,076,088 | A * | 6/2000 | Paik et al. ............................. | 1/1 |
| 6,675,159 | B1 * | 1/2004 | Lin et al. .............................. | 1/1 |
| 7,031,909 | B2 * | 4/2006 | Mao et al. ........................ | 704/9 |
| 7,809,548 | B2 * | 10/2010 | Mihalcea et al. ................. | 704/1 |
| 7,890,533 | B2 * | 2/2011 | Pollara .......................... | 707/790 |
| 7,899,666 | B2 * | 3/2011 | Varone .............................. | 704/9 |

(Continued)

OTHER PUBLICATIONS

Rada, R., Mili, H., Bicknell, E., and Blettner, M. (1989). Development and application of a metric on semantic nets. IEEE Transaction on Systems, Man, and Cybernetics, 19(1):17-30.*

(Continued)

*Primary Examiner* — Douglas Godbold  
*Assistant Examiner* — Michael Ortiz Sanchez  
(74) *Attorney, Agent, or Firm* — Mintz Levin Cohn Ferris Glovsky and Popeo, P.C.; Muriel Liberto, Esq.

(57) ABSTRACT

A method for performing natural language processing of free text using domain-specific spreading activation. Embodiments of the present invention ontologize free text using an algorithm based on neurocognitive theory by simulating human recognition, semantic, and episodic memory approaches. Embodiments of the invention may be used to process clinical text for assignment of billing codes, analyze suicide notes or legal discovery materials, and for processing other collections of text. Further, embodiments of the invention may be used to more effectively search large databases, such as a database containing a large number of medical publications.

19 Claims, 9 Drawing Sheets

(56) References Cited

U.S. PATENT DOCUMENTS

| | | | | |
|---|---|---|---|---|
| 8,145,716 | B2* | 3/2012 | Karamchedu et al. | 709/206 |
| 8,700,589 | B2* | 4/2014 | Tymoshenko et al. | 707/705 |
| 2002/0046259 | A1* | 4/2002 | Glorikian | 709/218 |
| 2002/0077810 | A1* | 6/2002 | Swinney | 704/201 |
| 2003/0217335 | A1* | 11/2003 | Chung et al. | 715/514 |
| 2004/0054744 | A1* | 3/2004 | Karamchedu et al. | 709/206 |
| 2005/0069936 | A1 | 3/2005 | Diamond et al. | |
| 2005/0278325 | A1* | 12/2005 | Mihalcea et al. | 707/6 |
| 2006/0031101 | A1* | 2/2006 | Ross | 705/3 |
| 2006/0092920 | A1* | 5/2006 | Karamchedu et al. | 370/352 |
| 2006/0129383 | A1 | 6/2006 | Oberlander et al. | |
| 2007/0213981 | A1 | 9/2007 | Meyerhoff et al. | |
| 2007/0294112 | A1* | 12/2007 | Settimi | 705/3 |
| 2007/0294113 | A1* | 12/2007 | Settimi | 705/3 |
| 2008/0275694 | A1* | 11/2008 | Varone | 704/9 |
| 2010/0169299 | A1* | 7/2010 | Pollara | 707/708 |
| 2010/0273153 | A1 | 10/2010 | Tabakoff et al. | |

OTHER PUBLICATIONS

Nigel Collier, et al., "Recent Advances in Natural Language Processing for Biomedical Applications", Int J Med Inform, Jun. 2006, pp. 413-417, vol. 75, No. 6, Shannon, Co. Clare: Elsevier Science Ireland Ltd., Ireland.

Daniel T. Heinze, PhD, et al., "Mining Free-Text Medical Records", Proceedings of the AMIA Symposium, Nov. 2001, pp. 254-258, Washington, D.C., U.S.A.

Alexander S. Yeh, et al., "Evaluation of Text Data Mining for Database Curation: Lessons Learned From the KDD Challenge Cup", Eleventh International Conference on Intelligent Systems for Molecular Biology, Jun.-Jul. 2003, pp. i331-i339, vol. 19, Brisbane, Australia.

Ariel S. Schwartz, et al., "A Simple Algorithm for Identifying Abbreviation Definitions in Biomedical Text", Pacific Symposium on Biocomputing, Jan. 2003, pp. 451-462, Lihue, Hawaii, U.S.A.

Jiri Hana, et al., "A Resource-light Approach to Russian Morphology: Tagging Russian using Czech Resources", Proc EMNLP Conf., Jul. 2004, pp. 222-229, Association for Computational Linguistics, Stroudsburg, PA, U.S.A.

Chris Brew, et al., "Spectral Clustering for German Verbs", Proc EMNLP Conf., Jul. 2002, pp. 117-124, Association for Computational Linguistics, Stroudsburg, PA, U.S.A.

Andrew Y. Ng, et al., "On Spectral Clustering: Analysis and an Algorithm", Proceedings of NIPS Conf., Oct. 2001, pp. 849-856, Vancouver, British Columbia, Canada.

Dan Klein, et al., "Corpus-Based Induction of Syntactic Structure: Models of Dependency and Constituency", Proceedings of the 42 Annual Meeting of the Association for Computational Linguistics, Jul. 2004, pp. 478-485, Barcelona, Spain.

Willem J. M. Levelt, "Producing Spoken Language: A Blueprint of the Speaker", The Neurocognition of Language, 1999, pp. 83-122, Ch. 4, Oxford University Press, London, Great Britain. [Month of publication is unknown. The year of publication is sufficiently earlier than the effective U.S. filing date and any foreign priority date so the particular month of publication is not in issue.].

C. Gerlach, et al., "Brain Activity Related to Integrative Processes in Visual Object Recognition: Bottom-up Integration and the Modulatory Influence of Stored Knowledge", Neuropsychologia, Dec. 2001, pp. 1254-1267, vol. 40, Issue 8, Pergamon Press, Oxford, England.

Terry L. Jernigan, et al., "Brain Activation During Word Identification and Word Recognition", Neuroimage, Jul. 1998, pp. 93-105, vol. 8, Article No. 1, Academic Press, Orlando, FL, U.S.A.

Elizabeth Madsen, BA, et al, "HIPAA Possumus", J Am Med Inform Assoc., May-Jun. 2003, p. 294, vol. 10, No. 3, Hanley & Belfus, Philadelphia, PA, U.S.A.

J. Decety, et al., "Brain Activity During Observation of Actions: Influence of Action Content and Subject's Strategy", Brain, Oct. 1997, pp. 1763-1777, vol. 120, Pt 10, Oxford University Press, Oxford, London, England.

George Mandler, "Recognizing: The Judgment of Previous Occurrence", Psychological Review, May 1980, pp. 252-271, vol. 87, No. 3, American Psychological Association, Inc., Washington, DC, U.S.A.

Endel Tulving, "How Many Memory Systems Are There?", American Psychologist, Apr. 1985, pp. 385-398, vol. 40, No. 4, American Psychological Association, Inc., Washington, DC, U.S.A.

Martin Volk, et al., "Semantic Annotation for Concept-Based Cross-Language Medical Information Retrieval", Int J Med Inform, Dec. 2002, pp. 97-112, vol. 67(1-3), Elsevier Science Ireland Ltd., Ireland.

Ricky K. Taira, Phd., et al., "Identification of Patient Name References within Medical Documents Using Semantic Selectional Restrictions", Proceedings of the AMIA Symp, Nov. 2002, pp. 757-761, San Antonio, Texas, U.S.A.

F. Crestani, "Application of Spreading Activation Techniques in Information Retrieval", Artificial Intelligence Review, 1997, pp. 453-482, vol. 11, Kluwer Academic Publishers, Netherlands. [Month of publication is unknown. The year of publication is sufficiently earlier than the effective U.S. filing date any foreign priority date so the particular month of publication is not in issue.].

Pawel Matykiewicz, et al., "Nonambiguous Concept Mapping in Medical Domain", Proceedings of the 8th International Conference of Artificial Intelligence and Soft Computing, Jun. 2006, pp. 941-950, Zakopane, Poland.

Handelman, et al., "The Content of Suicide Notes from Attempters and Completers," Crisis: The Journal of Crisis Intervention and Suicide Prevention, 2007, pp. 102-104, vol. 28, No. 3, Hogrefe & Huber Publishers, Cambridge, MA, US. [Month of publication is unknown. This is all the identifying information that is publicly available.].

Barr, et al., "Self-harm or attempted suicide? Do suicide notes help us decide the level of intent in those who survive?," Accident and Emergency Nursing, Jul. 2007, pp. 122-127, vol. 15, Issue 3, Elsevier, The Netherlands.

Freedenthal, Stacey, "Challenges in Assessing Intent to Die: Can Suicide Attempters be Trusted?," OMEGA, 2007, pp. 57-70, vol. 55, No. 1, Center for Palliative Care and Death Education, Baywood Publishing Co., Inc., Amityville, NY, US. [Month of publication is unknown. This is all the identifying information that is publicly available.].

Itert, et al., "Influence of a priori Knowledge on Medical Document Categorization," IEEE Symposium on Computational Intelligence and Data Mining, Apr. 2007, 8 pages, Honolulu, HI, US.

Rajan, et al., "Medical Acronym Disambiguation Using Online Sources," Conference on Enterprise Information Systems and Web Technologies, Jul. 2007, 8 pages, Orlando, FL, US.

Ruperto, et al., "The Paediatric Rheumatology International Trials Organization (PRINTO)," Lupus, Aug. 2007, pp. 670-676, vol. 16, No. 8, Sage Publications, Thousand Oaks, CA, US.

Gerstein, et al., "What is a gene, post-ENCODE? History and updated definition," Genome Research, Jun. 2007, pp. 669-681, vol. 17, No. 6, Cold Spring Harbor Laboratory Press, Cold Spring Harbor, NY, US.

Maletic, et al., "Neurobiology of depression: an integrated view of key findings," International Journal of Critical Practice, Dec. 2007, pp. 2030-2040, vol. 61, No. 12, Blackwell Publishing Ltd., John Wiley & Sons, Hoboken, NJ, US.

Siest, et al., "Pharmacogenenomique et pharmacoproteomique: Strategie pour les medicaments cardio-vasculaires," Annales Pharmaceutiques Francaises, May 2007, vol. 65, Issue 3, pp. 203-210, Elsevier Masson SAS, Issy les Moulineaux Cedex, France.

Pestian, et al., "A Shared Task Involving Multi-label Classification of Clinical Free Text," BioNLP 2007: Biological, translational, and clinical language processing, Association for Computational Linguistics, Jun. 2007, pp. 97-105, Prague, Czech Republic.

Duch, et al., "Towards Understanding of Natural Language: Neurocognitive Inspirations," Part II of the Proceedings of 17th International Conference on Artificial Neural Networks, Lecture Notes in Computer Science, Sep. 2007, pp. 953-962, Porto, Portugal.

Duch, et al., "Neurolinguistic Approach to Vector Representation of Medical Concepts," Proceedings of the International Joint Conference on Neural Networks, Aug. 2007, 6 pages, Orlando, Florida, US.

Caporaso, et al., "Rapid Patterns Development for Concept Recognition Systems: Application to Point Mutations," Journal of

(56) References Cited

OTHER PUBLICATIONS

Bioinformatics and Computational Biology, Dec. 2007, pp. 1233-1259, vol. 5, No. 6, Imperial College Press, London, Great Britain, United Kingdom.
Pestian, et al., "Using Natural Language Processing to Classify Suicide Notes," Proceedings of BioNLP 2008: Current Trends in Biomedical Natural Language Processing, Association for Computation Linguistics, Jun. 2008, pp. 96-97, Columbus, Ohio, US.
Lei Mo, et al., "Brain Activation During Semantic Judgment of Chinese Sentences: A Functional MRI Study", Hum Brain Mapp, Apr. 2005, pp. 305-312, vol. 24, Issue 4, Wiley-Liss, Inc., New York, NY, U.S.A.
Mohamed L. Seghier, et al., "Variability of fMRI Activation During a Phonological and Semantic Language Task in Healthy Subjects", Hum Brain Mapp, Nov. 2004, pp. 140-155, vol. 23, Issue 3, Wiley-Liss, Inc., New York, NY, U.S.A.
Susan L. Rossell, et al., "Brain Activation During Automatic and Controlled Processing of Semantic Relations: A Priming Experiment using Lexical-Decision", Neuropsychologia, Aug. 2001, pp. 1167-1176, vol. 39, Issue 11, Elsevier, The Netherlands.
Jörg D. Jescheniak, et al., "Semantic and Phonological Activation in Noun and Pronoun Production", The Journal of Experimental Psychology: Learning, Memory, and Cognition, Jul. 2001, pp. 1058-1078, vol. 27, Issue 4, American Psychological Association, Inc., Washington, DC, U.S.A.
Manfred Herrmann, et al., "Control of Semantic Interference in Episodic Memory Retrieval is Associated with an Anterior Cingulate-Prefrontal Activation Pattern", Hum Brain Mapp, Jun. 2001, pp. 94-103, vol. 13, Issue 2, Wiley-Liss, Inc., New York, NY, U.S.A.
Zellig S. Harris, "The Structure of Science Information", Journal of Biomedical Informatics, Aug. 2002, pp. 215-221, vol. 35, Issue 4, Academic Press, San Diego, CA, U.S.A.
Carol Friedman, PhD, et al., "A General Natural-Language Text Processor for Clinical Radiology", Journal of the American Medical Informatics Association, Mar./Apr. 1994, pp. 161-174, vol. 1, Issue 2, Hanley & Belfus, Philadelphia, PA, U.S.A.
Carol Friedman, et al., "Two Biomedical Sublanguages: A Description Based on the Theories of Zellig Harris", Journal of Biomedical Informatics, Aug. 2002, pp. 222-235, vol. 35, Issue 4, Academic Press, San Diego, CA, U.S.A.
Naomi Sager, PhD, et al., "Natural Language Processing and the Representation of Clinical Data", Journal of the American Medical Informatics Association, Mar./Apr. 1994, pp. 142-160, vol. 1, Issue 2, Hanley & Belfus, Philadelphia, PA, U.S.A.
Jianguo Li, et al., "Robust Extraction of Subcategorization Data from Spoken Language", Proceedings of the Ninth International Workshop on Parsing Technologies, Oct. 2005, pp. 204-205, Association for Computational Linguistics, Vancouver, British Columbia, Canada.
Chris Brew, "Language Processing, Statistical Methods", Feb. 2005, pp. 1-10, retrieved from www.ling-ohio-state.edu/~cbrew/lpsm.pdf on Jun. 15, 2012.
Simone Teufel, "Argumentative Zoning for Improved Citation Indexing", Jul. 2004, Computing Attitude and Affect in Text: Theory and Applications, pp. 159-170, Springer, Dordrecht, The Netherlands.
Hiyan Alshawi, et al., "CLARE: A Contextual Reasoning and Cooperative Response Framework for the Core Language Engine", Dec. 1992, pp. 1-272, SRI International, Cambridge, UK.
Eric Brill, "Unsupervised Learning of Disambiguation Rules for Part of Speech Tagging", Natural Language Processing using Very Large Corpora, 1995, pp. 1-13, vol. 30, Association for Computational Linguistics, Springer, Germany. [Month of publication is unknown. The year of publication is sufficiently earlier than the effective U.S. filing date and any foreign priority date so the particular month of publication is not in issue.].
J.-D. Kim, et al., "GENIA Corpus—A Semantically Annotated Corpus for Bio-Textmining", Eleventh International Conference on Intelligent Systems for Molecular Biology, Jul. 2003, pp. i180-i182, vol. 19, Suppl. 1, Brisbane, Australia.
Fabio Crestani, et al., "Searching the Web by Constrained Spreading Activation", Information Processing & Management, Jul. 2000, pp. 585-605, vol. 36, Issue 4, Pergamon Press, Inc. Oxford, England.
Yoshimasa Tsuruoka, et al., "Developing a Robust Part-of-Speech Tagger for Biomedical Text", 10th Panhellenic Conference on Informatics, Nov. 2005, pp. 382-392, vol. 3746, University of Thessaly, Volos, Greece.
Mirella Lapata, et al., "Verb Class Disambiguation using Informative Priors", Computational Linguistics, Mar. 2004, pp. 45-73, vol. 30, No. 1, MIT Press, Cambridge, MA, U.S.A.
Wlodzislaw Duch, et al., "Towards Avatars with Artificial Minds: Role of Semantic Memory", Memory, Jan. 2007, 10 pp, vol. 5, American Scientific Publishers, Valencia, CA, U.S.A.
Kristina Toutanova, et al., "Feature-Rich Part-of-Speech Tagging with a Cyclic Dependency Network", Proceedings of the 2003 Conference on the North American Chapter of the Association of Computational Linguistics on Human Language Technology, May 2003, pp. 173-180, vol. 1, Edmonton, California, U.S.A.
Janet Holmes, et al., "Inferring Language Change from Computer Corpora: Some Methodological Problems", ICAME Journal No. 18, Apr. 1994, pp. 27-40, International Computer Archive of Modern English, Bergen, Norway.
"Appendix B: Sample Text That Can Be Used to Clarify Public Health Issues Under the Privacy Rule", Morbidity and Mortality Weekly Report, May 2003, pp. 19-20, vol. 52, No. 1, http://www.cdc.gov/mmwr/preview/mmwrhtml/su5201a3.htm, Centers for Disease Control and Prevention, U.S.A.
David A. Campbell, et al., "Comparing Syntactic Complexity in Medical and Non-Medical Corpora", Proceedings of AMIA Symposium, Nov. 2001, pp. 90-94, Washington, D.C., U.S.A.
Rosalind Raine, et al., "An Experimental Study of Determinants of Group Judgments in Clinical Guideline Development", Lancet, Jul./Aug. 2004, pp. 429-437, vol. 364, No. 9432, Lancet Publishing Group, London, England.
D J W Hunter, et al., "Appropriate Indications for Prostatectomy in the UK—Results of a Consensus Panel", J Epidemiology and Community Health, Feb. 1994, pp. 58-64, vol. 48, Issue 1, British Medical Assn., London, England.
E A Scott, et al., "Appropriateness of Cholecystectomy in the United Kingdom—A Consensus Panel Approach", Gut, Sep. 1991, pp. 1066-1070, vol. 32, Issue 9, British Medical Assn., London, England.
Susan E. Ziemba, M.D., et al., "Resting Electrocardiograms as Baseline Tests: Impact on the Management of Elderly Patients", Am J Med, Dec. 1991, pp. 576-583, vol. 91, Issue 6, Donnelly, New York, NY, U.S.A.
Edward H. Giannini, et al., "A Validated Disease Severity Scoring System for Fabry Disease", Molecular Genetics and Metabolism, Mar. 2010, pp. 283-290, vol. 99, Issue 3, Academic Press, Orlando, FL, U.S.A.
Mathew H. Liang, M.D., et al., "The Total Hip Arthroplasty Outcome Evaluation Form of the American Academy of Orthopaedic Surgeons", J Bone Joint Surg Am., Jun. 1991, pp. 639-646, vol. 73, Issue 5, Journal of Bone and Joint Surgery, Incorporated, Boston, MA, U.S.A.
John S. Justeson, et al., "Principled Disambiguation: Discriminating Adjective Senses With Modified Nouns", Journal Computational Linguistics, Mar. 1995, pp. 1-27, vol. 21, Issue 1, MIT Press, Cambridge, MA, U.S.A.
Michael Krauthammer, et al., "Term Identification in the Biomedical Literature", Journal of Biomedical Informatics, Dec. 2004, pp. 512-526, vol. 37, Issue 6, Academic Press, San Diego, CA, U.S.A.
Thomas C. Rindflesch, et al., "Medical Facts to Support Inferencing in Natural Language Processing", Proceedings of the American Medical Informatics Association Annual Symposium, Oct. 2005, pp. 634-638, Washington, D.C., U.S.A.
Minsuk Lee, et al., "Exploring Supervised and Unsupervised Methods to Detect Topics in Biomedical Text", BioMedCentral Bioinformatics, Mar. 2006, 11 pages, vol. 7, No. 140, BioMed Central Ltd., London, England.
Leanne M. Currie, et al., "Development and Representation of a Fall-Injury Risk Assessment Instrument in a Clinical Information System", Stud Health Technol Inform, 2004, pp. 721-725, vol. 107, Pt. 1, IOS Press, Amsterdam, Netherlands. [Month of publication is

(56) References Cited

OTHER PUBLICATIONS unknown. The year of publication is sufficiently earlier than the effective U.S. filing date and any foreign priority date so the particular month of publication is not in issue.].

Christopher J. O. Baker, et al., "Mutation Mining—A Prospector's Tale", Information Systems Frontiers, Feb. 2006, pp. 47-57, vol. 8, No. 1, Springer, Germany.

Florence Horn, et al., "Automated Extraction of Mutation Data from the Literature: Application of MuteXt to G Protein-Coupled Receptors and Nuclear Hormone Receptors", Bioinformatics, Mar. 2004, pp. 557-568, vol. 20, Issue 4, Oxford University Press, Oxford, England.

Aurélie Névéol, et al., "Automatic Indexing of Specialized Documents: Using Generic vs. Domain-Specific Document Representations", Biological Translational and Clinical Language Processing, Jun. 2007, pp. 183-190, Association for Computational Linguistics, Stroudsburg, PA, U.S.A.

Christian Blaschke, et al., "Automatic Extraction of Biological Information from Scientific Text: Protein-Protein Interactions", Proceedings of the International Conference Intelligent Systems for Molecular Biology, Aug. 1999, pp. 60-67, Heidelberg, Germany.

Soumya Ray, et al., "Learning Statistical Models for Annotating Proteins with Function Information using Biomedical Text", BMC Bioinformatics, May 2005, 5 pp, vol. 6, Suppl 1, BioMed Central, London, England.

Illhoi Yoo, et al., "A Coherent Biomedical Literature Clustering and Summarization Approach Through Ontology-Enriched Graphical Representations", Lecture Notes in Computer Science, Data Warehousing and Knowledge Discovery, Sep. 2006, pp. 374-483, vol. 4081, Krakow, Poland.

Illhoi Yoo, et al., "A Comprehensive Comparison Study of Document Clustering for a Biomedical Digital Library MEDLINE", Proceedings of the 6th ACM/IEEE-CS Joint Conference on Digital Libraries, Jun. 2006, pp. 220-229, ACM, Chapel Hill, NC, U.S.A.

Craig A. Struble, et al., "Clustering MeSH Representations of Biomedical Literature", HLT-NAACL '04, May 2004, pp. 41-48, Association for Computational Linguistics, Boston, MA, U.S.A.

A. Hotho, et al., "Ontology-Based Text Clustering", Proceedings of Seventeenth International Joint Conference on Artificial Intelligence, IJCAI '01, Aug. 2001, 8 pages, Seattle, Washington, U.S.A.

Allan M. Collins, et al., "A Spreading-Activation Theory of Semantic Processing", Psychological Review, Nov. 1975, pp. 407-428, vol. 82, Issue 6, American Psychological Assoc., Washington, DC, U.S.A.

Scott K. Holland, et al., "Functional MRI of Language Lateralization During Development in Children", Int J Audiol, Sep. 2007, pp. 533-551, vol. 46, Issue 9, BC Decker, Hamilton, Ont., England.

P. R. Karunanayaka, et al., "Age Related Connectivity Changes in fMRI Data from Children Listing to Stories", Proceedings of the 14th Annual Meeting and Exhibition of the International Society of Magnetic Resonance in Medicine, May 2006, p. 3287, vol. 14, Seattle, Washington, U.S.A.

Stanislas Dehaene, et al., "The Neural Code from Written Words: A Proposal", TRENDS in Cogn Sci, Jul. 2005, pp. 335-341, vol. 9, Issue 7, Elsevier Science, Kidlington, Oxford, UK, England.

Diego A. Preciado, et al., "A Diagnostic Paradigm for Childhood Idiopathic Sensorineural Hearing Loss", Otolaryngol Head Neck Surg., Dec. 2004, pp. 804-809, vol. 131, Issue 6, Sage Publications, Thousand Oaks, CA, U.S.A.

Diego A. Preciado, et al., "Improved Diagnostic Effectiveness with a Sequential Diagnostic Paradigm in Idiopathic Pediatric Sensorineural Hearing Loss", Otol Neurotol, Jul. 2005, pp. 610-615, vol. 26, Issue 4, Lippincott Williams & Wilkins, Philadelphia, PA, U.S.A.

S. Wiley, et al., "GJB2 Mutations and Additional Disabilities in a Pediatric Cochlear Implant Population", International Journal Pediatric Otorhinolaryngoly, Mar. 2006, pp. 493-500, vol. 70, Issue 3, Elsevier, The Netherlands.

David I. Bernstein, MD, et al., "Diisocyanate Asthma and Gene-Environment Interactions with IL4RA, CD-14, and IL-13 Genes", Annals of Allergy Asthma Immunology, Dec. 2006, pp. 800-806, vol. 97, Issue 6, American College of Allergy, Asthma, and Immunology, McLean, VA, U.S.A.

Ritesh Kaushal, et al. "Association of AL0X5AP with Ischemic Stroke: A Population-Based Case-Control Study", Hum Genet, Jun. 2007, pp. 601-607, vol. 121, Issue 5, Springer-Verlag, Berlin, Germany.

Ge Zhang, et al., "Statistical Power of Association Using the Extreme Discordant Phenotype Design", Pharmacogenet and Genomics, Jun. 2006, pp. 401-413, vol. 16, Issue 6, Lippincott Williams & WilkinsHagerstown, MD, U.S.A.

Dennis W. McGraw, et al., "Crosstalk Between Gi and Gq/Gs Pathways in Airway Smooth Muscle Regulates Bronchial Contractility and Relaxation", J Clin Invest, May 2007, pp. 1391-1398, vol. 117, Issue 5, American Society for Clinical Investigation, New Haven, U.S.A.

Kersten M. Small, et al., "$\alpha$2A- and $\alpha$2C-Adrenergic Receptors form Homo- and Heterodimers: The Heterodimeric State Impairs Agonist-Promoted GRK Phosphorylation and $\beta$-Arrestin Recruitment", Biochemistry, Apr. 2006, pp. 4760-4767, vol. 45, Issue 15, American Chemical Society, Washington, U.S.A.

Kersten M. Small, et al., "Complex Haplotypes Derived from Noncoding Polymorphisms of the Intronless $\alpha$2A-Adrenergic Gene Diversify Receptor Expression", Proc Natl Acad Sci U.S.A., Apr. 2006, pp. 5472-5477, vol. 103, Issue 14, The National Academy of Sciences, Washington, DC, U.S.A.

Martin J Ronis, et al., "Altered Expression and Glucocorticoid-Inducibility of Hepatic CYP3A and CYP2B Enzymes in Male Rats Fed Diets Containing Soy Protein Isolate", J Nutr, Nov. 1999, pp. 1958-1965, vol. 129, Issue 11, American Society for Nutritional Sciences, Bethesda, MD, U.S.A.

Simone Gupta, et al., "Pharmacogenomics: A Path to Predictive Medicine for Schizophrenia", Pharmacogenomics, Jan. 2006, pp. 31-47, vol. 7, No. 1, Future Medicine Ltd., London, England.

Gérard Siest, et al., "Pharmacogenomics and Cardiovascular Drugs: Need for Integrated Biological System with Phenotypes and Proteomic Markers", European Journal of Pharmacology, Dec. 2005, pp. 1-22, vol. 527, Issue 1-3, Elsevier, The Netherlands.

Sridhar Prathikanti, et al., "Psychiatric Genetics—The New Era: Genetic Research and Some Clinical Implications", British Medical Bullitin, Dec. 2005, pp. 107-122, vol. 73 and 74, Oxford University Press, London, England.

Lisa G. Rider, et al., "Development of Validated Disease Activity and Damage Indices for the Juvenile Idiopathic Inflammatory Myopathies", Arthritis & Rheumatism, Nov. 1997, pp. 1976-1983, vol. 40, Issue 11, Arthritis Foundation, Atlanta, U.S.A.

Lisa G. Rider, et al., "International Consensus on Preliminary Definitions of Improvement in Adult and Juvenile Myositis", Arthritis & Rheumatism, Jul. 2004, pp. 2281-2290, vol. 50, Issue 7, Arthritis Foundation, Atlanta, U.S.A.

Carol A. Wallace, et al., "Patterns of Clinical Remission in Select Categories of Juvenile Idiopathic Arthritis", Arthritis & Rheumatism, Nov. 2005, pp. 3554-3562, vol. 52, Issue 11, Arthritis Foundation, Atlanta, U.S.A.

Edward H. Giannini, et al., "Preliminary Definition of Improvement in Juvenile Arthritis", Arthritis & Rheumatism, Jul. 1997, pp. 1202-1209, vol. 40, Issue 7, Arthritis Foundation, Atlanta, U.S.A.

Nicolino Ruperto, et al., "Preliminary Core Sets of Measures for Disease Activity and Damage Assessment in Juvenile Systemic Lupus Erythematosus and Juvenile Dermatomyositis", Rheumatology, Dec. 2003, pp. 1452-1459, vol. 42, Issue 12, Oxford University Press, Oxford, Great Britain, United Kingdom.

Thorsten Brants, "TnT—A Statistical Part-of-Speech Tagger", Proceedings of the Sixth Conference on Applied Natural Language Processing, Apr. 29-May 4, 2000, pp. 224-231, Association for Computational Linguistics, Seattle, Washington, U.S.A.

Lawrence Hunter, et al., "OpenDMAP: An Open Source, Ontology-Driven Concept Analysis Engine, with Applications to Capturing Knowledge Regarding Protein Transport, Protein Interactions and Cell-Type-Specific Gene Expression", BMC Bioinformatics, Jan. 2008, 11 pages, vol. 9, Issue 78, BioMed Central, London, Great Britain, United Kingdom.

(56) References Cited

OTHER PUBLICATIONS

Zhiyong Lu, et al., "Finding GeneRIFs Via Gene Ontology Annotations", Pacific Symposium on Biocomputing 2006, Jan. 2006, pp. 52-63, Maui, Hawaii, U.S.A.

Zhiyong Lu, et al., "GeneRIF Quality Assurance as Summary Revision", Pacific Symposium on Biocomputing 2007, Jan. 2007, pp. 269-280, Maui, Hawaii, U.S.A.

John P. Pestian, et al., "A Shared Task Involving Multi-Label Classification of Clinical Free Text", Proceedings of the Workshop on BioNLP 2007: Biological, Translational, and Clinical Language Processing, Jun. 2007, p. 97-104, Association for Computational Linguistics, Prague, Czech Republic.

Wlodzislaw Duch, et al., "Towards Understanding of Natural Language: Neurocognitive Inspirations", Proceedings of the International Conference on Artificial Neural Networks, ICANN 2007, 17th International Conference, Sep. 2007, pp. 953-962, Porto, Portugal.

Susan Bookheimer, "Functional MRI of Language: New Approaches to Understanding the Cortical Organization of Semantic Processing", Annu Rev Neurosci, Mar. 2002, pp. 151-188, vol. 25, Annual Reviews, Inc., Palo Alto, CA, U.S.A.

Michael T. Ullman, "A Neurocognitive Perspective on Language: The Declarative/Procedural Model", Nature Review Neuroscience, Oct. 2001, pp. 717-726, vol. 2, Issue 10, Nature Pub. Group, New York, NY, U.S.A.

Uta Frankenstein, et al., "Activation and Deactivation in Blood Oxygenation Level Dependent Functional Magnetic Resonance Imaging", Concepts in Magnetic Resonance, Jan. 2003, pp. 63-70, vol. 16A, Issue 1, John Wiley and Sons, Ltd., Hoboken, NJ, U.S.A.

Monika-Zita Zempleni, "Evidence for Bilateral Involvement in Idiom Comprehension: An fMRI Study", Neuroimage, Feb. 2007, pp. 1280-1291, vol. 34, Issue 3, Academic Press, Orlando, FL, U.S.A.

J. Richard Landis, et al., "The Measurement of Observer Agreement for Categorical Data", Biometrics, Mar. 1977, pp. 159-174, vol. 33, Issue 1, Biometric Society, Alexandria, VA, U.S.A.

Hans Van Halteren, et al., "Improving Data Driven Wordclass Tagging by System Combination", Proceedings of the 36th Annual Meeting of Association for Computational Linguistics, Aug. 1998, pp. 491-497, vol. 1, University of Montreal, Montreal, Quebec, Canada.

R. M. A. Nelissen, et al., "Limitations of Semantic Priming Procedures for Automatic Goal Activation", Psychological Reports, Dec. 2005, pp. 675-689, vol. 97, Issue 3, Southern Universities Press, Louisville, KY, U.S.A.

Harold Burton, et al., "Visual Cortex Activation in Late-Onset, Braille Naive Blind Individuals: An fMRI Study During Semantic and Phonological Tasks With Heard Words", Neuroscience Letters, Jan. 2006, pp. 38-42, vol. 392, Issue 1-2, Elsevier, The Netherlands.

K. Bretonnel Cohen, et al., "A Resource for Constructing Customized Test Suites for Molecular Biology Entity Identification Systems", Human Language Technology Conference—NAACL '04, May 2004, pp. 1-8, Association for Computational Linguistics, Boston, MA, U.S.A.

Lukasz Itert, et al., "Medical Document Categorization using a Priori Knowledge", Proceedings of International Conference on Artificial Neural Networks, Sep. 2005, pp. 641-646, Warsaw, Poland.

Jeremy Jones, et al., "Consensus Methods for Medical and Health Services Research", British Medical Journal, Aug. 1995, pp. 376-380, vol. 311, No. 7001, BMJ Publishing Group Ltd, London, Great Britain, United Kingdom.

William A. Baumgartner, Jr., et al., "An Integrated Approach to Concept Recognition in Biomedical Text", Genome Biology: The BioCreative II, Sep. 2008, vol. 9, Supp. 2, BioMed Central Ltd., London, Great Britain, United Kingdom.

Anne M. Libby, PhD., et al., "Decline in Treatment of Pediatric Depression after FDA Advisory on Risk of Suicidality with SSRIs", Am J Psychiatry, Jun. 2007, pp. 884-891, vol. 164, No. 6, American Psychiatric Association, Arlington, VA, U.S.A.

Peter M. Lewinsohn, et al., "Psychosocial Risk Factors for Future Adolescent Suicide Attempts", Journal or Consulting and Clinical Psychology, Apr. 1994, pp. 297-305, vol. 62, Issue 2, The American Psychological Association, Washington, DC, U.S.A.

Ann Tieleman, et al., "Stimulus Pacing Affects the Activation of the Medical Temporal Lobe During a Semantic Classification Task: An fMRI Study", NeuroImage, Jun. 2005, pp. 565-572, vol. 26, Issue 2, Academic Press, Orlando, FL, U.S.A.

Serguei V. Pakhomov, et al., "Developing a Corpus of Clinical Notes Manually Annotated for Part-of-Speech", Int J Medical Informatics, Jun. 2006, pp. 418-429, vol. 75, Issue 6, Elsevier Science Ireland, Ireland.

Mark Craven, et al., "Constructing Biological Knowledge Bases by Extracting Information from Text Sources", Proceedings of the Seventh International Conference on Intelligent Systems for Molecular Biology, Aug. 1999, pp. 77-86, Heidelberg, Germany.

G Ferraccioli, "Pharmacogenetic of Antirheumatic Treatments: Clinical Implications", Pharmacogenomics J, Feb. 2007, pp. 2-9, vol. 7, Issue 1, Nature Publishing Group, Avenet, NJ, U.S.A.

Joseph L. Fleiss, "Measuring Nominal Scale Agreement among Many Raters", Psychological Bulletin, Nov. 1971, pp. 378-382, vol. 76, No. 5, American Psychological Association, Washington, DC, U.S.A.

John P. Pestian, et al., "Preparing Clinical Text for Use in Biomedical Research", Journal of Database Management, Apr.-Jun. 2006, pp. 1-11, vol. 17, Issue 1, Idea Group Inc., Hershey, PA, U.S.A.

Landis, et al., "The Measurement of Observer Agreement for Categorical Data, Biometrics," Mar. 2007, pp. 159-174, vol. 33, No. 1, International Biometrics Society, Washington, D.C., US.

Hawton, et al., "Hospital Admissions for Adverse Effects of Medicinal Agents (Mainly Self-Poisoning) Among Adolescents in the Oxford Region," British Journal of Psychiatry, Aug. 1982, pp. 166-170, vol. 141, No. 2, The Royal College of Psychiatrists, London, Great Britain, United Kingdom.

Cohen, et al., "Information Retrieval by Constrained Spreading Activation in Semantic Networks, Information Processing and Management," Jul. 1987, pp. 255-268, vol. 23, No. 4, Pergamon Journals, Oxford, Great Britain, United Kingdom.

Schiel, Ulrich, "Abstractions in Semantics Networks: Axiom Schemata for Generalization, Aggregation and Grouping," SIGART Newsletter, Jan. 1989, pp. 25-26, No. 107, Association for Computing Machinery, New York, NY, US.

Brevard, et al., "A Comparison of Suicide Notes Written by Suicide Completers and Suicide Attempters," Crisis: The Journal of Crisis Intervention and Suicide Prevention, 1990, pp. 7-11, vol. 11, No. 1, Hogrefe & Huber Publishers, Cambridge, MA, US. [Month of publication is unknown. The year of publication is sufficiently earlier than the effective U.S. filing date and any foreign priority date so the particular month of publication is not in issue.].

Brill, Eric, "Discovering the Lexical Features of a Language," Proceedings of the 29th Annual Meeting on the Association for Computational Linguistics, Jun. 1991, pp. 339-340, Berkeley, CA, US.

Eddy, David, "Decisions Without Information: The Intellectual Crisis in Medicine," HMO Practice, 1991, pp. 58-60, vol. 5, Issue 2, HMO Practice, Buffalo, NY, US. [Month of publication is unknown. The year of publication is sufficiently earlier than the effective U.S. filing date and any foreign priority date so the particular month of publication is not in issue.].

Shneidman, Edwin, "Commentary: Suicide as Psychache," The Journal of Nervous and Mental Disease, Mar. 1993, pp. 145-147, vol. 181, No. 3, Wolters Kluwer Health, Riverwoods, IL, US.

Ozcan, et al., "The Effect of a Competency-based Targeted Staff Development Program on Nursing Productivity,"Journal of Nursing Staff Development, 1993, pp. 78-84, vol. 9, No. 2, Lippincott Williams & Wilkins, Philadelphia, PA, US. [Month of publication is unknown. The year of publication is sufficiently earlier than the effective U.S. filing date and any foreign priority date so the particular month of publication is not in issue.].

Nordstrom, et al., "CSF 5-HIAA predicts suicide risk after attempted suicide," Suicide & Life-Threatening Behavior, 1994, pp. 1-9, vol. 24, No. 1, The American Association for Suicidology, Washington, D.C., US. [Month of publication is unknown. The year of publication is sufficiently earlier than the effective U.S. filing date and any foreign priority date so the particular month of publication is not in issue.].

Scheidman, Edwin, "Clues to suicide, reconsidered," Suicide & Life-Threatening Behavior, 1994, pp. 395-397, vol. 24, No. 4, The Ameri-

(56) References Cited

OTHER PUBLICATIONS can Association for Suicidology, Washington, D.C., US. [Month of publication is unknown. The year of publication is sufficiently earlier than the effective U.S. filing date and any foreign priority date so the particular month of publication is not in issue.].

Shaffer, et al., "Psychiatric Diagnosis in Child and Adolescent Suicide," Arch Gen Psychiatry, Apr. 1996, pp. 339-348, vol. 53, American Medical Association, Chicago, IL, US.

Griffiths, et al., "Episodic memory: what can animals remember about their past?," Trends in Cognitive Sciences, Feb. 1999, pp. 74-80, vol. 3, No. 2, Elsevier, The Netherlands.

Mann, John J., "The neurobiology of suicide, Nature Medicine," Jan. 1998, pp. 25-30, vol. 4, No. 1, The Nature Publishing Group, New York, NY, US.

Brent, et al., "Age- and Sex-Related Risk Factors for Adolescent Suicide," Journal of American Academy of Child Adolescent Psychiatry, Dec. 1999, pp. 1497, vol. 38, No. 12, The American Academy of Child and Adolescent Psychiatry, Washington, D.C., US.

Kiefer, et al., "The course of conscious and unconscious semantic brain activation," Cognitive Neuroscience, NeuroReport, Aug. 2000, pp. 2401-2407, vol. 11, No. 11, Lippincott Williams & Wilkins, Philadelphia, PA, US.

Pedersen, Ted, "An Ensemble Approach to Corpus-Based Word Sense Disambiguation," 2000, 14 pp., University of Minnesota, Duluth, MN, US. [Month of publication is unknown. The year of publication is sufficiently earlier than the effective U.S. filing date and any foreign priority date so the particular month of publication is not in issue.].

Salib, et al., "The significance of suicide notes in the elderly, Aging & Mental Health," 2002, pp. 186-190, vol. 6, No. 2, Brunner Routledge Taylor & Francis Health Sciences, London, Great Britain, United Kingdom. [Month of publication is unknown. The year of publication is sufficiently earlier than the effective U.S. filing date and any foreign priority date so the particular month of publication is not in issue.].

Pandey, et al., "Higher Expression of Serotonin 5-HT2a Receptors in the Postmortem Brains of Teenage Suicide Victims," American Journal of Psychiatry, Mar. 2002, pp. 419-429, vol. 159, No. 3, American Psychiatric Association, Arlington, VA, US.

Salib, et al., "Their Last Words: A review of suicide notes in the elderly," Medicine, Science and the Law, 2002, pp. 334-338, vol. 42, No. 4, Royal Society of Medicine, London, Great Britain, United Kingdom. [Month of publication is unknown. The year of publication is sufficiently earlier than the effective U.S. filing date and any foreign priority date so the particular month of publication is not in issue.].

Mann, J. John, "Neurobiology of Suicidal Behaviour," Neuroscience, Nature Reviews, Oct. 2003, pp. 819-828, Nature Publishing Group, New York, New York, US.

Mitchell, et al., "Implementation and Evaluation of a Negation Tagger in a Pipeline-based System for Information Extraction from Pathology Reports," Medinfo 2004: Proceedings of the 11th World Congress on Medical Informatics, Sep. 2004, pp. 663-667, IOS Press, Amsterdam, The Netherlands.

Valente, Sharon M., "Comparison of Suicide Attempters and Completers," Medicine and Law, 2004, pp. 693-714, vol. 23, World Association for Medicine and Law, Ghent, Belgium. [Month of publication is unknown. The year of publication is sufficiently earlier than the effective U.S. filing date and any foreign priority date so the particular month of publication is not in issue.].

Bridge, et al., "Adolescent Suicide and suicidal behavior, Journal of Child Psychology and Psychiatry," Mar./Apr.2006, pp. 372-394, vol. 47, No. 3, Issue 4, Association for Child and Adolescent Mental Health, Blackwell Publishing, Malden, MA, US.

Matykiewicz, et al., "Nonambiguous Concept Mapping in Medical Domain," Proceedings of Artificial Intelligence and Soft Computing—ICAISC 2006, 8th International Conference, Jun. 2006, Zakopane, Poland.

Mukherjea, Sougata, "Information retrieval and knowledge discovery utilising a biomedical Semantic Web," Briefings in Bioinformatics, Sep. 2005, pp. 252-262, vol. 6, No. 3, Henry Stewart Publications LLP, London, Great Britain, United Kingdom.

Shneidman, Edwin, "How I Read," Suicide and Life-Threatening Behavior, Apr. 2005, pp. 117-120, vol. 35, Issue 2, American Association of Suicidology, Washington, D.C., US.

Samuelsson, et al., "CSF 5-HIAA, suicide intent and hopelessness in the prediction of early suicide in male high-risk suicide attempters," Acta Psychiatrica Scandinavica, Jul. 2006, pp. 44-47. vol. 113, Blackwell Munksgaard, Frederiksberg, Denmark.

Anisman, et al., "Cytokines as a Precipitant of Depressive Illness: Animal and Human Studies," Current Pharmacological Design, 2005, pp. 963-972, vol. 11, Bentham Science Publishers Ltd., Sharjah, U.A.E. [Month of publication is unknown. The year of publication is sufficiently earlier than the effective U.S. filing date and any foreign priority date so the particular month of publication is not in issue.].

Itert, et al., "Medical Document Categorization Using a priori knowledge," ICANN 2005, International Conference on Artificial Neural Networks, Sep. 2005, pp. 641-646, Warsaw, Poland.

Garabik, Radovan, Editor, "Computer Treatment of Slavic and East European Languages," Proceedings of Third International Seminar of SLOVKO, Nov. 2005, 245 pp., Slovak National Corpus, Bratislava, Slovakia.

Feldman, et al., "A Cross-Language Approach to Rapid Creation of New Morpho-syntactically Annotated Resources," Proceedings of LREC 2006, International Conference on Language Resources and Evolution, May 2006, Genoa, Italy.

Helmut Schmid, "Probabilistic Part-of-Speech Tagging Using DecisionTrees", Proceedings of International Conference on New Methods in Language Processing, Center for Computational Linguistics, Sep. 1994, pp. 44-49, vol. 12, Issue 4, University of Manchester Institute of Science and Technology, Manchester, Great Britain.

S. E. Robertson, et al., "Probabilistic Models of Indexing and Searching", Proceedings of 4th Annual Conference of Special Information Group on Information Retrieval, May/Jun. 1981, pp. 35-56, Oakland, California, U.S.A.

Latanya Sweeney, et al., "Replacing Personally-Identifying Information in Medical Records, The Scrub System", Proceedings of the AMIA Fall Symposium, Oct. 1996, pp. 333-337, Hanley & Belfus, Inc., Philadelphia, PA, U.S.A.

Latanya Sweeney, "Weaving Technology and Policy Together to Maintain Confidentiality", Journal of Law, Medicine & Ethics, Jun. 1997, pp. 98-110, vol. 25, Issue 2-3, American Society of Law, Medicine and Ethics, Boston, MA, U.S.A.

C.T. Yu, et al., "A Generalized Term Dependence Model in Information Retrieval", Technical Report, Feb. 1983, URL: http://hdl.handle.net/1813/6383, Cornell University, Ithaca, NY, U.S.A. [Link is inactive. The document was retrieved by client sufficiently earlier than the effective U.S. filing date and any foreign priority date so the particular month of publication is not in issue.].

Helmut Berger, et al., "An Adaptive Information Retrieval System Based on Associative Networks", Proceedings of Asia-Pacific Conference on Conceptual Modeling, Jan. 2004, pp. 27-36, vol. 31, Dunedin, New Zealand.

Fabio Crestani, "Retrieving Documents by Constrained Spreading Activation on Automatically Constructed Hypertexts", Proceedings of EUFIT 97—Fifth European Conference on Intelligent Techniques and Soft Computing, Sep. 1997, pp. 91-114, vol. 1, Issue 1-2, Aachen, Germany.

W. Bruce Croft, "Approaches to Intelligent Information Retrieval", Information Processing & Management, Jul. 1987, pp. 249-254, vol. 23, No. 4, Elsevier Ltd., The Netherlands.

Vijay V. Raghavan, et al., "A Critical Analysis of Vector Space Model for Information Retrieval", J Am Soc Inform Science, Sep. 1986, pp. 279-287, vol. 37, Issue 5, John Wiley & Sons, Inc., New York, NY, U.S.A.

W.B. Croft, et al., "Retrieving Documents by Plausible Inference: A Preliminary Study", Proceedings of the 10th Annual ACM SIGIR Conference on Research and Development in Information Retrieval, Jun. 1988, pp. 481-494, Grenoble, France.

W. B. Croft, et al., "Retrieving Documents by Plausible Inference: An Experimental Study", Information Processing & Management, 1989,

(56) References Cited

OTHER PUBLICATIONS pp. 599-614, vol. 25, Issue 6, Pergamon Press plc, Great Britain. [Month of publication is unknown. The year of publication is sufficiently earlier than the effective U.S. filing date and any foreign priority date so the particular month of publication is not in issue.].

W.B. Croft, et al., "I3R: A New Approach to the Design of Document Retrieval Systems", J Am Soc Inform Science, Nov. 1987, pp. 389-404, vol. 38, Issue 6, John Wiley & Sons, Inc., New York, NY, U.S.A.

K. Hartmann, et al., "A Spreading Activation Approach to Text Illustration", Int. Symp. on Smart Graphics, Jun. 2002, pp. 39-46, ACM, New York, NY, U.S.A.

Jonghoon Lee, et al., "Context-Sensitive Vocabulary Mapping With a Spreading Activation Network", Proceedings of the 22nd Annual International ACR SIGIR Conference of Research and Development in Information Retrieval, Aug. 1999, pp. 198-205, University of California, Berkeley, California, U.S.A.

Cristiano Rocha, et al., "A Hybrid Approach for Searching in the Semantic Web", Proceedings of the International World Wide Web Conference, May 2004, pp. 374-383, ACM, New York, NY, U.S.A.

Deanna M. Barch, et al., "Semantic Priming in Schizophrenia: An Examination of Spreading Activation Using Word Pronunciation and Multiple SOAs", Journal of Abnormal Psychology, Nov. 1996, pp. 592-601, vol. 105, Issue 4, American Psychological Association, Inc., Washington, DC, U.S.A.

Gordon J. Harris, et al., "Brain Activation During Semantic Processing in Autism Spectrum Disorders Via Functional Magnetic Resonance Imaging", Brain and Cogn, Jun. 2006, pp. 54-68, vol. 61, Issue 1, Academic Press, New York, NY, U.S.A.

David Blacker, et al., "Differential Activation of Frontal Lobe Areas by Lexical and Semantic Language Tasks: A Functional Magnetic Resonance Imaging Study", J Clin Neurosci, Jan. 2006, pp. 91-95, vol. 13, Issue 1, Churchill Livingstone, Edinburgh, Scotland.

Eliane C. Miotto, et al., "Bilateral Activation of the Prefrontal Cortex After Strategic Semantic Cognitive Training", Hum Brain Mapp, Apr. 2006, pp. 288-295, vol. 27, Issue (4), Wiley-Liss, Inc., New York, NY, U.S.A.

Chandler, et al., "Personal Persistence, Identity Development, and Suicide: A Study of Native and Non-Native North American Adolescents" In press, Monographs of the Society for Research in Child Development, pp. 1-75, Apr. 2003, Monographs of the Society for Research in Child Development, Canada.

Mossner, et al., "Consensus Paper of the WFSBP Task Force on Biological Markers: Biological Markers in Depression", The World Journal of Biological Psychiatry, Jan. 2007, pp. 141-174, col. 8(3), Taylor & Francis, United Kingdom.

Shen, et al., "Dimensional Complexity and Spectral Properties of the Human Sleep EEG", Clinical Neurophysiology, Feb. 2003, pp. 199-209, vol. 114, Elsevier, The Netherlands.

Robin, et al., "Bioinformatics for Protein Biomarker Panel Classification: What is needed to bring Biomarker Panels into in vitro Diagnostics", Expert Rev Proteomics, Dec. 2009, pp. 675-689, 6(6), Future Science Group, United Kingdom.

Reynolds, et al., "Assessment of Suicidal Ideation in Inner-City Children and Young Adolescents: Reliability and Validity of the Suicidal Ideation Questionnaire-JR", School Psychology Review, 1999, pp. 17-30, vol. 28, No. 1, National Association of School Psychologists, Bethesda, Maryland, USA.

Liu, et al., "Association of TPH 1 with Suicidal Behaviour and Psychiatric Disorders in the Chinese Population", Journal of Medical Genetics, Feb. 2006, pp. 1-6, vol. 43, Issue 2, BMJ Publishing Group Ltd, United Kingdom.

Williams, "The Relationship among Linguistic Patterns, Thwarted Belongingness, Perceived Burdensomeness, and Suicidal Behavior: A Test of Joiner's Theory of Suicide", phD Thesis, Mar. 2006, pp. 1-103, Florida State University, Florida, USA.

Non-Final Office action, U.S. Appl. No. 13/266,272, filed Oct. 26, 2011, mailed on Nov. 8, 2013, 59 pgs., United States Patent & Trademark Office, Alexandria, Virginia, USA.

\* cited by examiner

1 YEAR OLD FEMALE WITH ASTHMA, FEVER, AND UPPER RESPIRATORY INFECTION, TO EVALUATE FOR PNEUMONIA. TWO VIEWS OF THE CHEST SHOW NO FOCAL OPACITY TO INDICATE CONSOLIDATION OR ATELECTASIS . THE LUNGS BE CLEAR . THE HEART, MEDIASTINUM, AND PLMONARY VASCULATURE BE NORMAL. THE MEDIAL PORTION OF THE RIGHT HEMIDIAGPHRAGM APPEARS PROMINENT, WHICH CAN BE DUE TO EVENTRATION OR CAN BE A NORMAL ANATOMICAL VARIANT . THE BONE AND SOFT TISSUE BE NORMAL . NO FOCAL PNEUMONIA.

FIG. 1

MANUAL UMLS CONCEPT ONTOLOGIZER FOR GRAPHS OF CONSISTENT CONCEPTS
OUR TARGET: CREATE A LEARNING SET THAT WILL TEACH AN EXPERT SYSTEM TO
AUTOMATICALLY ANNOTATE A MEDICAL PATIENT DATA

PREV | 16 | PREV | JOHN PESTIAN ▶

PRIOR STUDY HAVE SHOW PERIBRONCHIAL THICKENING AND ATELECTASIS WITH VIRAL DISEASE
PLEASE PERFORM A FOLLOW - UP STUDY PERIBRONCHIAL THICKENING HAVE SIGNIFICANTLY
IMPROVE SINCE THE 12/16/04 *STUDY* NO *FOCAL CONSOLIDATION* BE *IDENTIFY*. THE *INCREASED*
*ATTENTUATION IN THE LINGULA* HAVE *RESOLVE* . 1 . *MARKED IMPROVEMENT IN PERIBRONCHIAL*
*THICKENING* COMPARE TO THE 12/16/04 *STUDY* NO *FOCAL CONSOLIDATION BE SEE* . 2.
PERIBRONCHIAL *THICKENING* HAVE ALSO *IMPROVE* COMPARE TO THE 3/11/04 *STUDY* . *PERSISTENT*
*MILD BILATERAL PERIBRONCHIAL THICKENING BE LIKELY RELATED TO A RECENT VIRAL ILLNESS*
DOCUMENT ON THE 12/16/04 *STUDY* . *I SUSPECT* THAT *NOT ENOUGH TIME HAVE ELAPSE*
*BETWEEN THAT STUDY AND THE CURRENT STUDY FOR THE PATIENT TO HAVE REACH*
*A COMPLETELY NORMAL BASE - LINE* . HOWEVER *I DO NOT SUSPECT SIGNIFICANT*
CHRONIC DISEASE ON

THE *BASIS OF THIS STUDY*
NONE OF THE MENTIONED (NONE)
IMPROVED (QUALITATIVE CONCEPT) ← 208
ATTENUATED BY (QUALITATIVE CONCEPT)

← 206

ABOUT AUTHOURS: PAWEL MATYKIEWIEZ, WLODZISLAW DUCH, JOHN PESTIAN.

PLEASE CHOOSE THE MOST SPECIFIC CONCEPTS.
WHEN YOU ARE FINISHED SIMPLY CLOSE THE WEB-PAGE.

FIG. 4

COMPARISON OF DISAMBIGUATION

|  | TRAINING | |
| --- | --- | --- |
|  | CORPUS I | CORPUS II |
| CORPUS I | 96% | 86% |
| CORPUS II | 64% | 79% |

FIG. 7

PROCESSING TEXT WITH DOMAIN-SPECIFIC SPREADING ACTIVATION METHODS

CROSS REFERENCE TO RELATED APPLICATIONS

This application claims the benefit of U.S. Provisional Application No. 60/878,718, filed Jan. 4, 2007, which is incorporated by reference in its entirety.

BACKGROUND

This invention relates to natural language processing and, more specifically, to a method for performing natural language processing of free text using domain-specific spreading activation.

SUMMARY

Embodiments of the present invention provide a computerized system and method for performing natural language processing of free text using domain-specific spreading activation. Embodiments of the present invention ontologize free text using an algorithm based on neurocognitive theory by simulating human recognition, semantic, and episodic memory approaches. Embodiments of the invention may be used to process clinical text for assignment of billing codes, analyze suicide notes or legal discovery materials, and for processing other collections of text, for example. Further, embodiments of the invention may be used to more effectively search large databases, such as a database containing a large number of medical publications.

In a first aspect, a method for processing natural language may include the steps of providing a text, the text including a plurality of groups of characters; providing a database, the database including associations between a plurality of known words and a plurality of concepts, the database further including quantitative values, each quantitative value being representative of a strength of a relationship between a first one of the concepts and a second one of the concepts; identifying one or more of the plurality of groups of characters as corresponding to at least one of the plurality of known words; creating a list of the identified known words; querying the database to obtain a first set of concepts associated with each of the identified known words; and annotating the list of identified known words with the first set of concepts associated with each identified known word; querying the database to obtain a second set of concepts, each concept in the second set of concepts being associated with a concept in the first set of concepts; and annotating the list of identified words with the second set of concepts by considering the quantitative value representative of the strength of the relationship between each concept in the second set of concepts and its associated concept in the first set of concepts.

In a detailed embodiment of the first aspect, the method may include the step of preparing the text prior to the identifying step, the step of preparing the text including at least one of tagging parts of speech, replacing abbreviations with words, and correcting misspelled words. The method may include the step of providing an output including at least one of the concepts in the first set of concepts. The step of annotating the list of identified words with the second set of concepts may include removing from the second set of concepts any of the second set of concepts that have a quantitative value that is less than a predetermined threshold value. The text may include clinical free text, for example; and the clinical free text may include pediatric clinical free text. The text may include a plurality of documents and the method may further include the step of identifying a subset of the plurality of documents by identifying at least two documents having associations with at least one identical concept. The method may further include the step of producing an output, the output including identification of one or more portions of each of the at least two documents having associations with the at least one identical concept. The text may include at least one suicide note, for example, and the method may include the step of evaluating at least the first set of concepts for indications of suicidal intent.

In a second aspect, a computer implemented method for assigning a medical billing code may include the steps of comparing, by a computer, a passage against a first ontology to recognize specific medical concepts in the passage; creating, by the computer, a semantic network including specific medical concepts and related concepts; weighting, by the computer, relationships between the specific medical concepts and the related concepts, each relationship having a weight; identifying, by the computer, the specific medical concept or related concept having a heaviest weight; and comparing, by the computer, the specific medical concept or related concept having the heaviest weight against a second ontology to identify a billing code associated with that specific medical concept or related concept in the second ontology.

In a detailed embodiment of the second aspect, the step of creating, by the computer, a semantic network may include querying a database to obtain the related concepts; and the step of weighting, by the computer, relationships between the specific medical concepts includes the step of querying the database to obtain a weight for each relationship between the specific medical concepts and a weight for each relationship between the specific medical concepts and the related concepts. The method may include the step of, after the weighting step, removing from the semantic network any related concepts that have a weight that is less than a predetermined threshold value. The step of creating the semantic network may include a step of expanding the network by adding additional related concepts, the step of expanding the network ending when one of the weights falls below a predetermined threshold. The second comparing step may include the step of obtaining human assistance if the computer does not identify a billing code, the step of obtaining human assistance including transmitting the passage to a human professional, assigning by the human professional a billing code, and recording the assigned billing code to be associated with the specific medical concept or related concept with the heaviest weight, by the computer, into the ontology. The step of creating the semantic network may include a step of expanding the network by adding additional related concepts, the step of expanding the network ending when one of the weights falls below a predetermined threshold.

In a third aspect, a method for processing natural language may include the steps of providing a text containing natural language; tagging parts of speech in the text; recognizing known words in the text; creating a semantic network, the semantic network including at least one of the recognized known words and at least one relationship with at least one concept associated with at least one of the recognized known words; and supplementing the semantic network by adding additional concepts and additional relationships to the semantic network, each additional concept being associated with at least one of the concepts and each additional relationship connecting at least one of the concepts to at least one of the additional concepts.

In a detailed embodiment of the third aspect, the method may include the steps of weighting each of the at least one relationships and each of the additional relationships with a weighting value reflecting the strength of each relationship and additional relationship; determining a minimum threshold weighting value; and eliminating from the semantic network the relationships and the additional relationships that do not satisfy the minimum threshold weighting value. The method may include the steps of comparing the at least one concepts and the additional concepts to a list of known relevant concepts to generate a list of identified relevant concepts; and providing an output based on at least one of a number and a significance of the identified relevant concepts. The output may pertain to a probability of a particular occurrence. The text may include at least one suicide note and the particular occurrence is a suicide attempt. The text may include a plurality of documents and the method may include the steps of entering a query including a search concept; and displaying a list of documents including one or more of the plurality of documents that is associated with at least one of the concepts and the additional concepts that matches the search concept. The list of documents may be sorted by the weighting value pertaining to at least one relationship or additional relationship between the search concept and the corresponding recognized known word.

These and other features and advantages of the present invention will become apparent to those skilled in the art upon consideration of the following detailed description of preferred embodiments exemplifying the best mode of carrying out the invention as presently perceived. The drawings are only to serve for reference and illustrative purposes, and are not intended to limit the scope of the invention.

BRIEF DESCRIPTION OF THE SEVERAL VIEWS OF THE DRAWINGS

The detailed description particularly refers to the accompanying Figures in which:

FIG. 1 depicts an exemplary sample of clinical text;

FIG. 4 is a screen capture of an exemplary ontologizer computer program operating on an exemplary computerized system according to the exemplary embodiments;

FIG. 7 illustrates a chart providing disambiguation results of an exemplary study;

DETAILED DESCRIPTION

Figure 2:
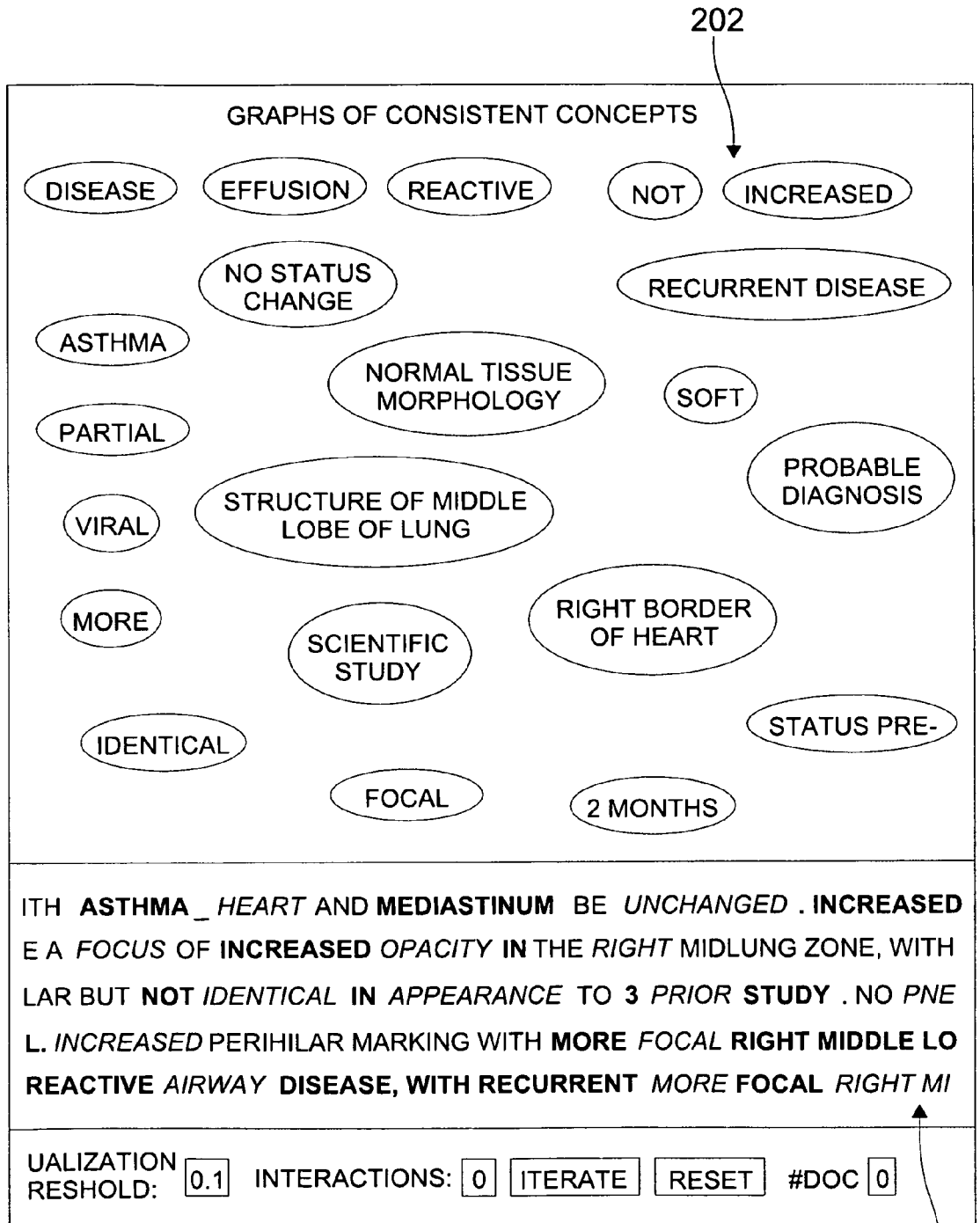
FIG. 2 depicts an exemplary normalized version of the text of FIG. 1 text with certain identified concepts highlighted in bold.

Embodiments of the present invention ontologize free text by using an algorithm based on neurocognitive theory. More specifically, embodiments of the present invention simulate human recognition, semantic and episodic memory approaches to ontologize text.

When embodiments of the present invention are applied in a computer to understand medical free text, for example, the first step is to teach an algorithm to recognize specific medical concepts that are found in an ontology (pneumonia for example). Next, the algorithm creates a semantic network of concepts related to pneumonia. For example, coughing, fever and chest x-ray may be related concepts. This semantic network can have many nodes or just a few. As the linking of the concepts spreads, the relationships between the concepts are quantified with some weight. At some point the weight becomes less than a predetermined threshold and the semantic network stops growing. This is because, if it were not constrained, the semantic network could grow endlessly. From this network the item with the heaviest weight is selected and a billing code that has already been integrated into the ontology (ontologies have relationships between concepts) is assigned. If the computer does not know what to do, it asks a Health Information Management professional to curate the data. The system learns from the HIM professional and remembers the correct coding result, thereby expanding its knowledge base. The entire cycle may be repeated for each new patient visit.

In other embodiments, the semantic network provides links to relevant information and concepts, such as the selection of appropriate drugs and dosages for certain diseases and conditions, analysis of suicide notes, and analysis of potentially large quantities of information, such as discovery information in a legal context.

Introduction

Multiple government agencies and numerous for-profit entities are collaborating to create a national health record that can be used by all caregivers. The hope is that a single medical record will be portable, reduce medical errors, avoid costly duplicate testing, and eliminate unnecessary hospitalizations. Its content, or the content of any medical records, can be classified into two general types of data: structured and unstructured. Structured data, such as laboratory results, have well-defined data types and clear semantics. These data have relevant cells of output from a particular test, and can be relied on to contain information in an expected way. By contrast, unstructured data, including such clinical free-text as transcribed discharge summaries, contain data whose interpretation may be substantially more challenging. Developing this electronic medical record is an enormous task and for the near future will probably focus on prescribing and laboratory data. See, e.g., Perlin J, Gelinas L. Workgroup: Electronic Health Record Laboratory Data Information Exchange. Paper presented at: American Health Information Community, 2006; Washington, D.C.

Unstructured data, however, cannot be ignored forever because it contains a tremendous amount of knowledge that is essential for care delivery. Moreover, with appropriate methods, this knowledge can be combined with genomic and proteomic data to form the information substrate necessary for personalized medicine. See, e.g., Collier N, Nazarenko A, Baud R, Ruch P. Recent Advances in Natural Language Processing for Biomedical Applications. *International Journal of Biomedical Informatics*. 2006; 75:413-417.

Unfortunately, this clinical free-text's lack of structure, heavy reliance on abbreviations, acronyms, medical jargon, redundancy, and ambiguity make it even more resistant to thorough analysis than, for example, newspaper text.

Attempts to mine clinical free-text have not been vacuous, as the potential value of these data is widely acknowledged.

These attempts have included: mining the data for quality of care purposes, administrative purposes, and scientific discovery. See, e.g., Heinze D T, Morsch M L, Hollbrook J. Mining Free-Text Medical Records. Paper presented at: AMIA, 2001; 2001; Yeh A, Hirschman L, Morgan A. Evaluation of Text Data Mining for Database Curation: Lessons Learned from the KDD Challenge Cup. *Bioinformatics.* 2003; 19(Supp 1):i331-i339; and Schwartz A, Hearst M. A Simple Algorithm for Identifying Abbreviation Definitions in Biomedical Texts. Paper presented at: Pacific Symposium on Biocomputing, 2003; Hawaii.

They have, however, had limited success for reasons related to the text, methods, or availability of training data. For definiteness, we assume that the prototypical instance of clinical free-text is a clinical note of some type; e.g., discharge summary that has been dictated by a physician-specialist, transcribed by a medical typist and is intended to be read by a second medical practitioner, perhaps the patient's primary care provider.

Our analysis indicates that automatically mining such text is challenging for three closely related reasons. First, medical providers will use the technical language that they know, a language that is filled with special terms. Second, clinical free-text is more like speech than text. Third, most Natural Language Processing (NLP) tools are tuned for newspaper text.

Despite these difficulties, the methods described herein provide unique advantages for mining clinical free-text because the rhetorical structure of clinical free-text is simpler than biomedical journals, the domain expertise is not infinite, existing NLP tools are trainable, and clinical free-text is holistic in nature, in the sense that decisions about how to interpret potentially ambiguous language are (or should be) linked by the common underlying influence of a hidden variable—the patient's state.

We believe that the human memory architecture provides a model for semantic processing of clinical free-text. The natural mode of human semantic interpretation will also work holistically under the assumption of simple underlying causes. The difficulty that we all experience in accepting or even understanding nuanced arguments is evidence of this assumption. Therefore, a goal of this invention is to enhance the accuracy of pediatric clinical free-text mining by developing domain specific spreading activation methods that mimic human memory models.

Spreading activation is a neuro-cognitive model that attempts to simulate human memory by creating networks of information, called semantic networks. This fundamental neuron-cognitive process and related computational approach are rarely acknowledged in the natural language processing of clinical free-text. Yet, it is reasonable to propose that by involving some form of artificial memory, e.g., recognition, semantic and/or episodic, clinical free-text can be mined more effectively.

Like other artificial intelligence methods, spreading activation relies on training corpora. Since annotation is costly, the methods of the present invention heuristically bootstrap valid corpus annotations by initially annotating smaller corpora; then relying on technology to extend the latter into heuristically valid annotations of a much larger corpus. For these efforts, two corpora can be developed using anonymized data. Linguists and clinicians operating in a careful system of quality control will create one corpus, the Cincinnati Pediatric Supervised Corpus (CPSC). Part-of-Speech (POS) quality will be monitored in formal reviews, and corrected as necessary. Unified Medical Language System (UMLS) concepts will be added to the Cincinnati Pediatric Unsupervised Corpus (CPUC). The CPUC is an existing corpus of 590,000 tokens that has been randomly selected from pediatric transcriptions, scrupulously anonymized and then semi-automatically annotated with POS labels. See, e.g., Pestian J P, Itert L, Meyer S. Development of the Cincinnati Pediatric Clinical Corpus. *International Journal of Biomedical Informatics.* 2006; Forthcoming.

An exemplary embodiment of the present invention may be adapted to achieve several goals. First, using our encryption broker and ontologizer software, develop a disambiguated an anonymous CPSC by reviewing and disambiguating 30-50 clinical documents from the following subspecialties: radiology, nephrology, pulmonary, behavioral medicine, psychiatry, rheumatology, pathology, cardiology, allergy and immunology, critical care, hematology/oncology, and human genetics.

Second, evaluate the quality of the CPUC's POS tagging. This can be done by a generalization of the methodology adopted in the Manchester tagger paper combined with techniques for using componential tags originally developed in by Feldman, Hana and Brew. See, e.g., Hana J, Feldman A, Brew C. Buy One Get One Free or What To Do When Your Linguist Resources are Limited. Paper presented at: International Seminar on Computer Treatment of Slavic and East-European Languages, 2004; Bratislava, Slovakia; Hana J, Feldman A, Brew C. A Resource-Light Approach to Russian Morphology Tagging Russian Using Czech Resources. Paper presented at: Conference on Empirical Methods in Natural Language Processing, 2004; Barcelona, Spain; and Feldman A, Hana J, Brew C. A Cross-Language Approach to Rapid Creation of New Morpho-Syntactically Annotated Resources. Paper presented at: Fifth International Conference on Language Resources and Evaluation, 2006; Genoa, Italy.

Third, use spreading activation methods to annotate the CPUC with UMLS concepts. The results of this can be evaluated using methods similar to those developed by Brew and Walde. See, e.g., Brew C, Walde SS. Spectral Clustering for German Verbs. Paper presented at: Conference on Empirical Methods in Natural Language Processing, 2002; Philadelphia, Pa.

Fourth, test the spreading activation method on anonymized clinical free-text. Then train the spreading activation tool with the developed corpora. Retest the same clinical free-text and compare results.

Fifth, evaluate neurocognition concept-mapping techniques, such as spreading-activation of semantic processing, against more traditional methods, such as template/relation extraction and spectral clustering. See, e.g., Brew C, Walde S S. Spectral Clustering for German Verbs. Paper presented at: Conference on Empirical Methods in Natural Language Processing, 2002; Philadelphia, Pa.; Ng A Y, Jordan M, Weiss Y. On Spectral Clustering: Analysis and an Algorithm. Paper presented at: Neural Information Processing Systems, 2002; Vancouver, British Columbia; and Klein D, Manning CD. Corpus-Based Induction of Syntactic Structure: Models of Constituency and Dependency. In: Cohen P, Clark A, Hovy E, Oates T, Witbrock M, eds. Language Learning: An Interdisciplinary Perspective. Stanford, Calif.; 2004.

Memory Models

Communication is a fundamental activity of human life. In all cultures, human bonding is achieved and maintained largely through speech (see, e.g., Levelt W J M. Producing Spoken Language: A Blueprint of the Speaker. In: Brown C M, Hagoort P, eds. The Neurocognition of Language. Oxford: Oxford University Press; 1999:83-122) and understanding that speech. After all, we are social animals, who deeply care for our closest kin and for unity in our daily personal contacts. Fundamental to communication is memory. Knowing the memory models and their theoretical underpinnings is basic to conducting research on memory-based information retrieval.

Comprehension and communication require various forms of memory. It is in memory that those who receive or send messages have the capacity to communicate by combining current and previous facts. A number of memory models have been studied over time; they can be divided in various ways, i.e., long and short-term memory, working memory, declarative memory, procedural memory or recognition memory, semantic memory and episodic memory. This description focuses on the last three and only those biological components that are germane to their computational modeling.

Recognition, Semantic and Episodic Memory

Recognizing elements in the environment, faces and places, as well as the ability to orient oneself within the environment are crucial to day-to-day functioning and navigation. Through recognition memory one identifies objects, words or actions. See, e.g., Gerlach C, Aaside C T, Humphreys G W, Gade A, Paulson O B, Law I. Brain activity related to integrative processes in visual object recognition: bottom-up integration and the modulatory influence of stored knowledge. Neuropsychologia. 2002; 40(8):1254-1267; Jernigan T L, Ostergaard A L, Law I, Svarer C, Gerlach C, Paulson O B. Brain activation during word identification and word recognition. NeuroImage. 1998; 8(1):93-105; and Decety J, Grezes J, Costes N, et al. Brain activity during observation of actions. Influence of action content and subject's strategy. Brain. 1997; 120(10):1763-1777.

Recognition memory is fundamental to our ability to remember. It requires a capacity both for identification and for judgment about the previous occurrence of what has been identified. See, e.g., Mandler G. Recognizing: The Judgment of Previous Occurrence. Psychological Review. 1980; 87:252-271.

Semantic memory and episodic memory are closely aligned. Semantic memory refers to the memory of meanings, understandings, and other factual knowledge. Semantic memory is a structured record of the facts, concepts and skills that we have acquired. The information in semantic memory is derived from the information in one's episodic memory, so that we can learn new facts or concepts from our experiences. See, e.g., Tulving E. How Many Memory Systems Are There? American Psychologist. 1985; 40:385-398.

Episodic memory is the recollection of events. It includes time, place, and associated emotions that affect the quality of memorization; episodic memory contrasts and interacts with semantic memory. Episodic memory is thought of as being a "one-shot" learning mechanism. You need only one exposure to an episode to remember it. Semantic memory, on the other hand, can take into consideration multiple exposures to each episode. For example, semantic memory indicates what a patient looks and sounds like. All episodic memories concerning that patient will refer to this single semantic representation, and conversely, all new episodes about that patient will modify the single representation of that patient. Some researchers believe that episodic memories are refined into semantic memories over time. Others believe that you always remember episodic events as episodic memories. See, e.g., Tulving E. Elements of Episodic Memory. Oxford: Clarendon Press; 1983; Encyclopedia WTF. Emotion and Episodic Memory. Wikimedia Foundation; and Griffiths D P, Dickson A, Clayton N S. Declarative and Episodic Memory: What Can Animals Remember About Their Past? Trends Cogn Sci. 1999; 3:74-80.

Using these components, a computer implemented schema for acquiring and understanding clinical free-text, for example, can be described. First, the computerized system recognizes the clinical free-text (recognition memory). The clinical free-text is then clustered into known concepts, say asthma or medications (semantic memory). Semantic memory determines if there are any episodes related to these concepts. If so, then the concept and episodes are linked together. For example, the patient's last visit for asthma treatment might be connected to the asthma concept and the patient's response to a specific medication might be connected to the medication concept. These connected concepts and episodes form a semantic network. Semantic memory then spreads to other concepts and episodes. For example, once the asthma concept is connected to the patient's last visit, there may be a recollection that this patient had a genetic test that indicated variants to the ADAM and PHF11 genes. This episode would then be connected to a secondary concept called asthma genetics, which would then be connected back to the patient via the asthma concept. This spreading will occur until, for some reason, it is stopped.

Semantic Networks

Semantic networks, originally introduced in 1968, have played a significant role in knowledge representation. See, e.g., Quillan R. Semantic Memory. In: Minsky M, ed. Semantic Information Processing. Cambridge: MIT Press; 1968: 216-270. According to Quillan's definition, semantic networks express knowledge in terms of concepts, their properties, and the hierarchical sub-superclass relationship among concepts. A node represents each concept. Connecting the concepts with a line that represents an "is-a" or "instance-of" link depicts the relationship between concepts. For example, sometimes asthma onset "is-a" response to environmental stresses like smoke. Since Quillan's definition, the term semantic network has come to be used in a far more general sense in the knowledge representation literature. Researchers have often used the term Semantic Network to refer to an Associative Network: a generic network of information items in which these items are represented by nodes, and links with undefined and unlabeled associative relations among the information items. When statistical techniques are used to associate weights to the links, a measure of the strength between associations is created thus, creating a semantic network. Processing semantic networks is usually done be means of spreading activation. See, e.g., Crestani F. Application of Spreading Activation Techniques in Information Retrieval. Artificial Intelligence Review. 1997; 11(6): 453-482.

Figure 3:
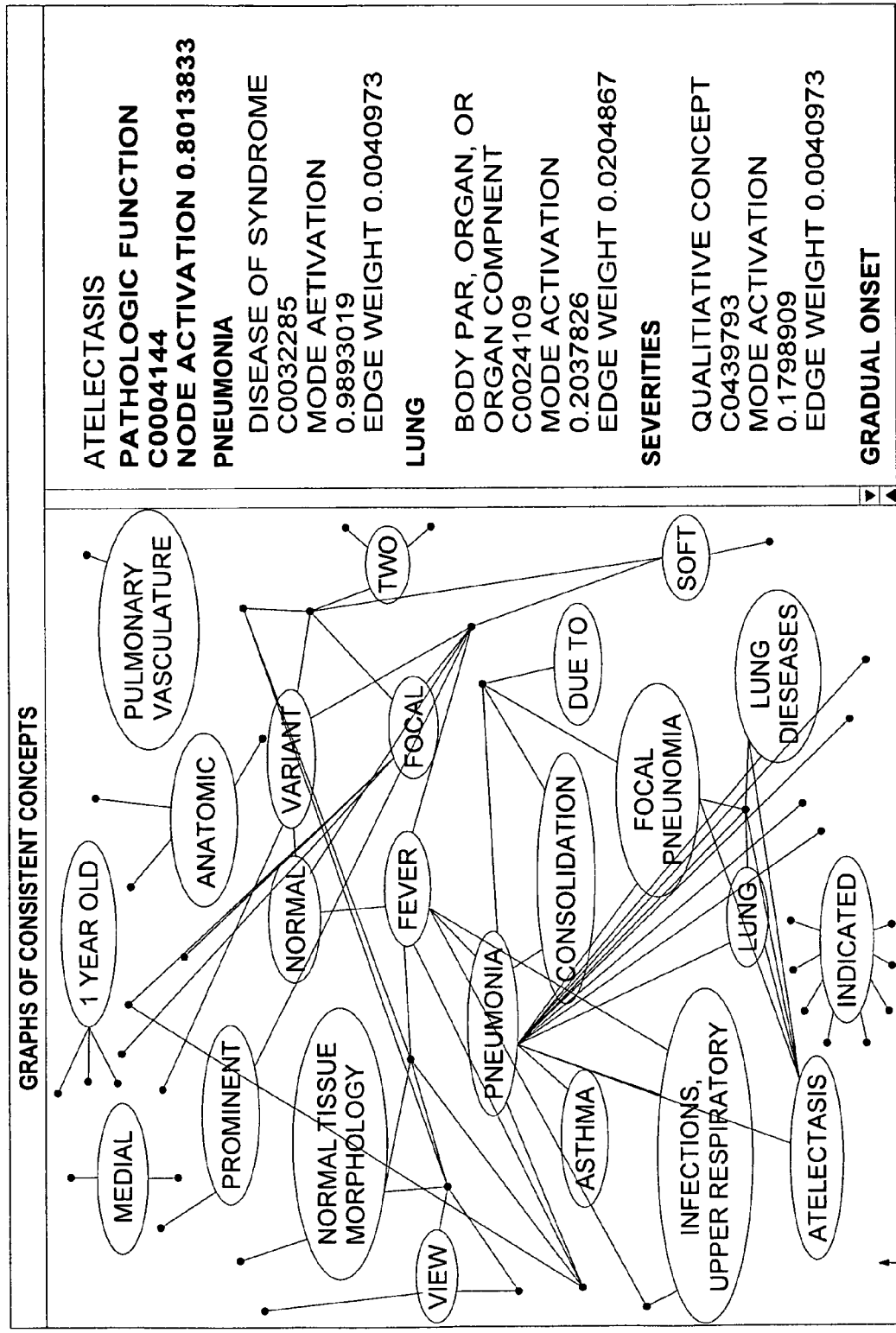
FIG. 3 depicts exemplary links between concepts.

FIGS. 1-3 provide a graphical representation of a semantic network that includes the memory models previously discussed. See, e.g., Matykiewicz P, Duch W, Pestian J P. Non-ambiguous Concept Mapping in a Medical Domain. Paper presented at: Artificial Intelligence and Soft Computing ICAISC, 2006; Poland. In FIG. 1, anonymous clinical text is presented. In FIG. 2, the normalized text 200 is shown, along with the concepts (highlighted in bold) that are found in the UMLS. Above the text, nodes 202 represent individual concepts, e.g., asthma; these nodes are labeled with the UMLS's text of the represented concept. At this point there are no semantic associations among nodes, and the only active concepts are those in the clinical free-text. FIG. 3 shows the links 204 between these concepts after the network has been iterated three times and a threshold of 0.1 is applied. That is, at iteration zero, concepts in the UMLS are identified in the clinical free-text if their weights meet the selected threshold. After that first iteration, the initial set of relationships is assigned to the initial concepts shown. This starts the spreading activation process. After the second iteration, additional concepts are selected if their weights meet the threshold. Any associated relationships are then assigned to the concept based on the results of the first iteration. After the third iteration, additional concepts are identified if their weights meet the selected threshold. Relationships are then assigned to these concepts based on the results of the second iteration.

The weights used in this process are based on the conditional probability of an concept $\chi$ occurring N times given the presence of $\chi$. Thus, $P(\Sigma\chi|\chi)$ For example, within the UMLS (version 2005AB) the concept of asthma has a Concept Identifier (CUI) of c004096. The UMLS has over 6,000 relationships to c004096. If the concept and its semantic network (represented by a matrix that is described in the Methods section) appeared only once then it would have a weight $P(1|6000)$ or 0.00016. On the other hand, if the concept and its semantic network appears 500 times, then the weight $P(500|6000)$ or 0.083. So, the relationship of 0.083 is greater than 0.00016. In the example in FIGS. 1-3, if the concept weight is greater than or equal to a pre-selected threshold, then the concept is considered sufficiently active to include it in the graph of consistent concepts. This example also highlights the importance of developing methods that limit the size of the semantic network by applying some constraints. Otherwise, the semantic network would always grow to its edges. The rules for constraining a semantic network are described under the Spreading Activation section. All conditional probabilities are pre-computed using the information from ULMS.

Spreading Activation

Spreading activation theory falls into the category of associative information retrieval. The idea behind this form of information retrieval is that it is possible to retrieve relevant information by retrieving information that is "associated" with information that the user has already retrieved and is known to be relevant. See, e.g., Crestani F. Application of Spreading Activation Techniques in Information Retrieval. Artificial Intelligence Review. 1997; 11(6):453-482. It is well known that simple matching procedures between the vocabularies contained in the query formulation and the stored documents do not always produce acceptable retrieval output. For that reason, some methods have been introduced to expand the query's formulation by adding to the initial queries new terms, or expressions that are related to the originally available terms. See, e.g., Salton G. Automatic Information Organization and Retrieval. New York: McGraw Hill; 1968 and Doyle L B. Information Retrieval and Processing. Los Angeles: Melville Publishing; 1975.

In principle, it is possible to use generally valid term or document associations for the expansion operation from say, an available term thesaurus. The term activation represents a numerical value intended to represent some aspect of the unit. The term spreading indicates that over time a unit's activation spreads to other units. For example, if the units in a model are terms related to psychiatric admissions to the hospital, the activation may be the probability that there are enough terms in a data file to indicate there is an extraordinary amount of psychiatric admissions.

Historically, other methods of computing locally valid terms and document associations have been attempted. They include such methods as the associative linear retrieval method, the maximum spanning tree of term similarities method, and the attempts to supply expanded document representations using citations and other bibliographic indicators attached to text and documents. See, e.g., Giulano V E, Jones P E. Linear Associative Information Retrieval. In: Howerton P, ed. Vistas in Information Handling. Washington, D.C.: Spartan Books; 1983; Robertson S E, van Rijsbergen C J, Porter M F. Probabilistic Models of Indexing and Searching. In: Oddy R N, Robertson C J, van Rijsbergen C J, Williams P W, eds. Information Retrieval Research. London: Buttersworth; 1981:33-56; and Fox E A. Extending the Boolean and Vector Space Models of Information Retrieval with P-Nor Queries and Multiple Concept Types. Ithaca: Computer Science, Cornell University; 1983.

The utility of these methods, however, has been limited for such reasons as: the inability to generalize the selected query terms, potentially correlated terms, potential dependence of one document on another thus, violating randomness, and the fact that simplified theoretical models may not reflect the reality of existing relationships between documents and terms in operational situations. See, e.g., Lesk M E. Word-word Associations in Document Retrieval Systems. American Documentation. 1989; 20(1):27-38; Raghavan V V, Wong S K M. A Critical Analysis of the Vector Space Model for Information Retrieval. Journal of American Society for Information Science. 1989; 37(5):279-287; and Yu C T, Buckley C, Lam K, Salton G. A Generalized Term Dependence Model in Information Retrieval. Information Technology: Research and Development. 1983; 2(4): 129-154.

Like the other methods, spreading activation networks were originally found to have a restricted utility, mainly for the reasons described above. See, e.g., Salton G, Buckley C. On the Use of Spreading Activation Methods in Automatic Information Retrieval. Ithaca: Cornell University; 1988. National Science Foundation Grant Number IRI 87-02735.

Spreading activation was then revised based on supposed mechanisms of human memory operations. Originating from psychological studies, it was first introduced in the area of artificial intelligence to provide a processing framework for semantic networks and has since been adopted by such areas as: cognitive science, databases, biology and information retrieval. See, e.g., Rumelhart D, Norman D. Representation in Memory: Technical Report. La Jolla: Psychology and Institute of Cognitive Science, UCSD; 1983. The basic spreading activation network model, however, requires domain expertise adaptations to make it more appropriate for domain specific applications.

How Spreading Activation Works

The spreading activation network model in its "pure" form utilizes a conceptually simple processing technique on a networked data structure. The networked data structure comprises nodes connected by links, as shown in FIG. 3. The nodes are usually labeled with the names of the objects they intend to represent. Representation between the objects, as shown by arrows, can be labeled or weighted. The structure has advantages because it could represent either a semantic network or an associative network. See, e.g., Crestani F. Application of Spreading Activation Techniques in Information Retrieval. Artificial Intelligence Review. 1997; 11(6): 453-482.

The spreading activation network processing technique comprises a sequence of iterations that continue until stopped by some termination requirement. Iterations include: at least one pulse—which is made of pre-adjustment, spreading and post-adjustment phases—and a termination check. See, e.g., Berger H, Dittenbach M, Merklm D. An Adaptive Information System Based on Associative Networks. Paper presented at: Proceedings of the first Asian-Pacific Conference on Conceptual Modeling, 2004; Dunedin, New Zealand.

During the pre and post adjustment phases, some type of decay function that weakens the relationship between nodes can be included. This approach implements a form of "loss of interest" in nodes that are not continually activated. As a result, links to these nodes in future iterations are not made.

The spreading phase includes a number of passages of activation that pulse from one node to all other nodes connected to it. Initially, an input value must be computed as shown in equation 1:

Equation 1. Spreading Activation Input Function $$I_j = \sum_i O_i w_{ij}$$

where:

$I_j$ is the total input of node j $O_i$ is the output of unit i connected to node j $w_{ij}$ is a weight associated to the link connecting node i to node j The inputs and the weight are usually real numbers. Their type, however, can be determined by the specific requirement of the application being modeled. For example, they can be binary (0 or 1), excitatory/inhibitory (+1 or −1), or real, to represent the strength of the relationships between nodes. Once a node's input has been calculated, the output value must be calculated. Like the input, the output's numerical type is determined by its application, with the two most frequent being binary or real weights. Since the output value is calculated based on a function of the input value, it is represented as shown in equation 2:

Equation 2. Spreading Activation Output Function $$O_j = f(I_j)$$

A number of different functions are available for evaluation of the output function. See, e.g., Crestani F. Retrieving Documents by Constrained Spreading Activation on Automatically Constructed Hypertext. Paper presented at: Proceedings of the EUFIT 98—Fifth European Congress on Intelligent Techniques and Soft Computing, 1997; Aachen, Germany. The threshold function, as shown in equation 3, is the function most commonly used in spreading activation networks. It is used to determine if the node j has to be considered active or not. The application of the threshold function in equation 2 in the case of binary value gives:

Equation 3. Spreading Activation Evaluation Function $$O_j = \begin{cases} 0 & I_j < k_j \\ 1 & I_j > k_j \end{cases}$$

where $k_j$ is the threshold value for unit j.

Like the other functions, the threshold value of the activation function is application-dependent and can vary from node to node, thus introducing the dependence of threshold on node, $k_j$. Once the output value is computed the node sends it to all other nodes connected to it, usually sending the same value to each of them. These pulses of spreading activation continue until some termination criterion is met. This process yields activation levels that are interpreted based on the application. In essence, this is a neural network model; although in real biological networks concepts are represented by the activation of a number of neural microcircuits. A single node representing a concept replaces an entire sub-network, and the links between the nodes estimate the transition probability between sub-networks, determining the strength of associations between concepts.

The pure spreading activation model, however, presents some difficulties:

Activation may spread over the entire network unless controlled carefully during the pre- and post-adjustment phases.

Information provided by the labels associated to the links is not fully used, i.e., there is no use of the semantics for the associations.

It is difficult to implement some form of inference based on the semantics of association.

Understanding the diverse relationship between nodes, or developing domain-specific methods for spreading, and using competition between the networked nodes can help solve these problems. For example, the information on the labels may be used to process links based on the label's semantics. Another way of restricting activation is to use various spreading constraint techniques such as: the distance, fan-out, path, and activation constraints. With the distance constraint, activation should cease when it reaches nodes that are far away in terms of the links covered to reach them. This constraint corresponds to the simple heuristic rule that the strength of the relationship decreases with increasing differences. With the fan-out constraint, spreading activation should cease at nodes with very high connectivity, i.e., fan-out to a large number of nodes. With path constraints, activation should spread using preferential paths, reflecting application-dependent inference rules. Finally, as in biological networks, where energy supply is limited, competition between the nodes leads to inhibition of nodes representing mutually exclusive interpretations, while activation constraints use a threshold function at a single node level to control spreading activation. See, e.g., Berger H, Dittenbach M, Merklm D. An Adaptive Information System Based on Associative Networks. Paper presented at: Proceedings of the first Asian-Pacific Conference on Conceptual Modeling, 2004; Dunedin, New Zealand.

Use of Spreading Activation

Spreading activation has received attention in a number of domains. Earlier works include Shoval's development of interactive query expansion based on a particular semantic network. See, e.g., Shoval P. Abstraction in Semantic Networks: Axiom Schemata for Generalization, Aggregation and Grouping. Paper presented at: Proceedings of ACM SIGIR, 1981.

GRANT, developed by Cohen and Kjeldsen, is a successful spreading activation system for information retrieval. GRANT organizes knowledge about research proposals and potential funding agencies by using a semantic network. From a heuristic point of view, GRANT can be considered an inference system. See, e.g., Cohen P, Kjeldesen R. Information Retrieval by Constraining Spreading Activation on Semantic Networks. Information Processing and Management. 1987; 23(4):255-268.

Croft designed the $I^3R$ system to study the possibility of retrieving documents by "plausible inference." This system was designed as a search intermediary that uses domain knowledge to infer concepts that are related to those mentioned in the query. A number of additional applications spawned from that research have focused on browsing techniques and how $I^3R$ could constrain spreading activation networks. See, e.g., Croft W. Approaches to Intelligent Information Retrieval. Information Processing and Management. 1987; 23(4):249-254; Croft W, Lucia T, Cohen P. Retrieving Documents by Plausible Inference: A Preliminary Study. Paper presented at: Proceedings of ACM SIGIR, 1988; Grenoble, France; Croft W, Lucia T, Cohen P, Willet P. Retrieving Documents by Plausible Inference: An Experimental Study. Information Processing and Management.

1989; 25(6):599-614; and Croft W, Thompson R H. I3R: A New Approach to the Design of Document Retrieval Systems. Journal of American Society for Information Science. 1987; 38(6):389-404.

More recently, spreading activation networks have been used to find information in text illustrations, context-sensitive vocabulary mapping, automatically constructed hypertext, and searching the semantic web. See, e.g., Crestani F. Retrieving Documents by Constrained Spreading Activation on Automatically Constructed Hypertext. Paper presented at: Proceedings of the EUFIT 98-Fifth European Congress on Intelligent Techniques and Soft Computing, 1997; Aachen, Germany; Hartman K, Strothotte T. A Spreading Activation Approach to Text Illustration. Paper presented at: Proceedings of the 2nd International Symposium on Smart Graphics, 2002; Hawthorne, N.Y.; Lee J, Dublin D. Context-Sensitive Vocabulary Mapping with a Spreading Activation Network. Paper presented at: Proceedings of the 22nd Annual International ACM SIGIR Conference on Research and Development in Information Retrieval, 1999; Hawthorne, N.Y.; and Rocha C, Schwage D, Poggi Aragao M. A Hybrid Approach for Searching in the Semantic Web. Paper presented at: International World Wide Web Conference, 2004; New York, N.Y.

Spreading activation has also been used in numerous brain modeling studies. They have included the use of spreading activation networks on word priming in schizophrenic patients, brain activation in autism disorders, frontal lobe activation, visual cortex activation, prefrontal activation, judgment, lexical neighbors, semantic priming, noun and pronoun production, episodic memory retrieval, age groups, and unconscious brain activation. See, e.g., Barch D, Cohen J, Servan-Schreiber D, Steingard S, Steinhauer S, van Kammen D. Semantic Priming in Schizophrenia: An Examination of Spreading Activation Using Word Pronunciation and Multiple SOAs. Journal of Abnormal Psychology. 1996; 105(4): 592-601; Nelissen R M, Dijker A J, de Vries N K. Limitations of semantic priming procedures for automatic goal activation. Psychol Rep. December 2005; 97(3):675-689; Harris G J, Chabris C F, Clark J, et al. Brain activation during semantic processing in autism spectrum disorders via functional magnetic resonance imaging. Brain Cogn. Feb. 10, 2006; Blacker D, Byrnes M L, Mastaglia F L, Thickbroom G W. Differential Activation of Frontal Lobe Areas by Lexical and Semantic Language Tasks: A Functional Magnetic Resonance Imaging Study. Journal of Clinical Neuroscience. January 2006; 13(1):91-95; Burton H, McLaren D G. Visual cortex activation in late-onset, Braille naive blind individuals: an fMRI study during semantic and phonological tasks with heard words. Neurosci Left. Jan. 9, 2006; 392(1-2):38-42; Miotto E C, Savage C R, Evans J J, et al. Bilateral activation of the prefrontal cortex after strategic semantic cognitive training. Hum Brain Mapp. April 2006; 27(4):288-295; Tieleman A, Seurinck R, Deblaere K, Vandemaele P, Vingerhoets G, Achten E. Stimulus pacing affects the activation of the medial temporal lobe during a semantic classification task: an fMRI study. NeuroImage. June 2005; 26(2):565-572; Mo L, Liu H L, Jin H, Yang Y L. Brain activation during semantic judgment of Chinese sentences: A functional MRI study. Hum Brain Mapp. April 2005; 24(4):305-312; Seghier M L, Lazeyras F, Pegna A J, et al. Variability of fMRI activation during a phonological and semantic language task in healthy subjects. Hum Brain Mapp. November 2004; 23(3):140-155; Rossell S L, Bullmore E T, Williams S C, David A S. Brain activation during automatic and controlled processing of semantic relations: a priming experiment using lexical-decision. Neuropsychologia. 2001; 39(11):1167-1176; Jescheniak J D, Schriefers H, Hantsch A. Semantic and phonological activation in noun and pronoun production. J Exp Psychol Learn Mem Cogn. July 2001; 27(4):1058-1078; Herrmann M, Rotte M, Grubich C, et al. Control of semantic interference in episodic memory retrieval is associated with an anterior cingulate-prefrontal activation pattern. Hum Brain Mapp. June 2001; 13(2):94-103; Toyota H. Changes in the semantic constraint of spreading activation of memory across three age groups. Percept Mot Skills. October 2000; 91(2):385-390; and Kiefer M, Spitzer M. Time course of conscious and unconscious semantic brain activation. Neuroreport. Aug. 3, 2000; 11(11):2401-2407.

Clinical Free-Text

In the delivery of clinical care, a detailed record of environmental information, diagnostic and therapeutic procedures, and economic information is kept on paper or in the form of electronic artifacts. At times, this information is from a structured vocabulary, such as responses to drop-down boxes in a clinical order entry menu, which are stored electronically. At other times, such information is clinical free-text that has been dictated by a caregiver and then transcribed onto the appropriate artifact. This clinical free-text is different from formally structured text, such as that found in manuscripts or abstracts. It has no formal structure and is heavily laden with specialty-specific jargon, abbreviations, and acronyms. See, e.g., Pestian J P, Itert L, Andersen C L, Duch W. Preparing Clinical Text for Use in Biomedical Research. Journal of Database Management. 2005; 17(2):1-12.

Moreover, NLP studies utilizing clinical free-text are still rare and require unavailable corpora including medical records. See, e.g., Collier N, Nazarenko A, Baud R, Ruch P. Recent Advances in Natural Language Processing for Biomedical Applications. *International Journal of Biomedical Informatics.* 2006; 75:413-417.

Some researchers, however, have indicated that there may be some structure to scientific communication, including clinical free-text. See, e.g., Carnap R. The Logical Syntax of Language. London: Kegan; 1934; Harris Z. The Structure of Science Information. J Biomed Inform. 2002; 35(4):215-221; Friedman C, Alderson P O, Austin J H, Cimino J J, Johnson S B. A general natural language text processor for clinical radiology. J Am Med Inform Assoc. March-April 1994; 1(2):161-174; Friedman C, Kra P, Rzhetsky A. Two biomedical sublanguages: a description based on the theories of Zellig Harris. J Biomed Inform. August 2002; 35(4):222-235; and Sager N, Lyman M, Bucknall C, Nhan N, Tick L J. Natural language processing and the representation of clinical data. J Am Med Inform Assoc. March-April 1994; 1(2):142-160.

These studies, however, have focused on clinical free-text with adult patients and not pediatric patients. Since many terms specific to pediatric care, e.g., tetralogy of fallot, are not specific to adult care and many terms specific adult care are not specific to pediatric care, e.g., myocardial infarction, there is no certainty that their results are generalizable to the pediatric setting.

Conducting NLP on clinical free-text presents a number of particular challenges:
  a) The text is generated by a medical practitioner for a medical practitioner, and assumes knowledge of medical terminology, concepts, and abbreviations.
  b) The text is informal, more like speech than written language, and it cannot be assumed that it has undergone a careful editorial process. Good medical typists may smooth out some infelicities, but they will also introduce errors not present in the original spoken text.
  c) With few exceptions (see, e.g., Tsuruoka Y, Tateishi Y, Kim J-D, et al. Developing a Robust Part-of-Speech Tagger for Biomedical Text. Lecture Notes in Computer Science: Springer; 2005:382-392.) the freely available tools that exist for NLP are tuned for newspaper text and have much higher error rate when applied to biomedical text. Recent work in Dr. Brew's lab offers potentially useful technology for handling the informality of the text, but much work remains. See, e.g., Li J, Brew C, Fosler-Lussier E. Robust Extraction of Subcategorization Data from Spoken Language. Paper presented at: Ninth International Workshop on Parsing Technology, 2005; Vancouver, British Columbia and Brew C. Language Processing: Statistical Methods. In: Brown K, ed. Encyclopedia of Language and Linguistics, 2nd Ed. Oxford: Elsevier; 2006.

Despite these difficulties, clinical free-text may prove more tractable than other text types:

1. The rhetorical structure of a clinical free-text may be considerably simpler than that of a biomedical journal article, for example. See, e.g., Teufel S. Argumentative Zoning for improved citation indexing. In: Shanahan J, Yan Q, Wiebe J, eds. Computing Attitude and Affect in Text: Theory and Applications. Dordrecht, The Netherlands: Springer; 2005:159-170. Feltrim V, Teufel S, Gracas-Nunes G, Alusio S. Argumentative Zoning applied to Critiquing Novices' Scientific Abstracts. In: Shanahan J, Yan Q, Wiebe J, eds. Computing Attitude and Affect in Text: Theory and Applications. Dordrecht, The Netherlands: Springer; 2005:233-245. The latter will often be making a complex argument, while the former is providing relatively concrete information about the patient and the medical team's assessment of what may need to happen next.
2. The background information that the writer of a clinical free-text may rely on is certainly technical in nature, but should not go significantly beyond what can be assumed from the generality of medical practitioners. This is important, because much of the relevant information is likely to be present in some form, either in the UMLS or similar resources. This is typically not true for journal articles, which typically involve hard-to-capture specialist terms. Regardless, clinical free-texts are a target of opportunity because of the good match to existing resources.
3. Existing NLP tools are trainable. Both the Manchester tagger and the TreeTagger can be tuned to new text-types by training against corpora. Even very small-annotated corpora of the right text type can make a big difference to performance. See, e.g., Tsuruoka Y, Tateishi Y, Kim J-D, et al. Developing a Robust Part-of-Speech Tagger for Biomedical Text. Lecture Notes in Computer Science: Springer; 2005:382-392.
4. The discharge summary is holistic in nature, in the sense that decisions about how to interpret potentially ambiguous language are (or should be) linked by the common underlying influence of a hidden variable—the patient's state. In word sense disambiguation, a one-sense-per-discourse heuristic has often proved fruitful, even for relatively complex texts. The present invention takes this approach further, by building heuristic models that are open to a wider range of linkages between the various decisions to be made.

Part-of-Speech Tagging

Part-of-speech tagging plays an important role in NLP. Obtaining the appropriate POS enables parsing for phrases and concepts within the text. The intent is to use POS for disambiguating clinical free-text. For example, the two sentences provide two different POS tags for the token patient.

Jane is a patient.
Jane is patient with her therapy.

In the first sentence patient is a noun, in the second it is an adjective. Based on the UMLS (2005AD) in the first sentence the concept would be patient; in the second sentence the concepts would be patient and therapy. Proper POS is essential for disambiguating text so concepts can be identified, but if POS tagging is used solely the results will be mixed.

One of the first studies to address the question of whether tagging helps in parsing was reported by Pulman in 1992. In this study, a tagger was trained on the Lancaster-Oslo/Bergen corpus and used as a preprocessor to the Core Language Engine. See, e.g., Pulman S. Using Tagging to Improve Analysis Efficiency. In: Thompson H, ed. SALT/ELSNET Workshop on Sub-language Grammar and Lexicon; 1992 and Alshawi H, Carter D, Crouch R, Pulman S, Rayner M, Smith A. CLARE: A Contextual Reasoning and Cooperative Response Framework for the Core Language Engine. Cambridge: SRI International; 1992. The process resulted in a loss of accuracy in parsing, though it did increase parsing speed. Accuracy was regained by the use of a multiple tagger, a tagger that returns more than one tag for each word. See, e.g., Pulman S. Using Tagging to Improve Analysis Efficiency. In: Thompson H, ed. SALT/ELSNET Workshop on Sub-language Grammar and Lexicon; 1992.

Subsequently, Wauschkuhn reported on a study of two German corpora; one was hand-tagged, and the other was statistically tagged, with an error rate of 3.5% to 4%. Both corpora were parsed twice: once with tags, and once without tags but with a morphological analyzer. No gold standard for either corpus existed, so the metric of success was the number of sentences receiving a single parse in each case. See, e.g., Wauschkuhn O. The Influence of Tagging on the Results of Partial Parsing in German Corpora. Paper presented at: Fourth International Workshop on Parsing Technologies, 1995; Karlovy Vary, Czech Republic. This study suffered from several problems. First, the tags assigned by the morphological analyzer did not correspond to the hand-tagged results, which made comparison of the results difficult. Second, it was not expected that tagging alone would completely disambiguate a sentence; sentences in clinical free-text may be structurally ambiguous, even with the same tags, so using a metric that defines success as obtaining a single parse does not seem appropriate. Third, the grammar used in the test seems quite small since the majority of sentences got either zero or one parse for both the tagged and the untagged corpus.

Artificial intelligence studies related to the use of unsupervised and supervised training have also been conducted. Brill (1995) presented a new algorithm for unsupervised training of a rule-based, POS tagger. The rule-based tagger trained using this algorithm significantly outperformed the traditional method of applying the Baum-Welch algorithm for unsupervised training of a stochastic tagger. Additionally, the authors have shown that combined unsupervised and supervised learning can develop a tagger that significantly outperforms a tagger trained using purely supervised learning. See, e.g., Brill E. Unsupervised Learning of Disambiguation Rules for Part of Speech Tagging. Paper presented at: Proceedings of the Third Workshop of Very Large Corpora, 1995. Pakhomov, et al. used three clinical domain experts to POS tag a corpus of clinical notes. These experts were able to accurately tag and use it for training English and Medical corpora. The accuracy of machine tagging for the English corpus was 89.79% and the Medical corpus was 94.69%. The authors indicated the necessity for adapting state-of-the-art POS taggers to the sublanguage domain of clinical text. See, e.g., Pakhomov S, Coden A, Chute C G. Developing a Corpus of Clinical Notes Manually Annotated for Part-of-Speech. International Journal of Medical Informatics. 2006; 75(6): 418-429.

Confidentiality

Clinical free-text artifacts will usually also be considered highly confidential and presently must meet the security requirements of the Health Insurance Portability and Accountability Act of 1996. See, e.g., Madsen E, Masys D R, Miller R A. HIPPA Possumus. J Am Med Inform Assoc. May-June 2003; 10(3):294. Both manual and automated attempts have been made to make these data confidential without losing their contextual value; retaining contextual value is important for research on natural language. For example, Pestian et al. reviewed 71,000 clinical trigrams from pediatric discharge summaries and surgical notes to develop rules for normalizing, anonymizing and converting abbreviations and acronyms into clinical free-text. This analysis yielded 350 specific expert rules, a database of female and male first names, a database of surnames and software for processing the clinical free-text. These data and the software are entitled the Encryption Broker ("EB").

The EB was tested on 1,000,000 clinical free-text tokens. The results indicated that while the rule based system was particularly good at normalizing the clinical free-text, converting abbreviations and acronyms to full text, and anonymizing patient and physician names, it did not do as well in anonymizing specific geographical concepts, e.g., the west side of town. In fact, after manually reviewing the original 1,000,000 tokens 410,000 tokens were removed so that confidentiality would not be violated. The final results created the Cincinnati Unsupervised Pediatric Corpus. See, e.g., Pestian J P, Itert L, Meyer S. Development of the Cincinnati Pediatric Clinical Corpus. *International Journal of Biomedical Informatics.* 2006; Forthcoming and Pestian J P, Itert L, Andersen C L, Duch W. Preparing Clinical Text for Use in Biomedical Research. Journal of Database Management. 2005; 17(2):1-12. It is quite plausible that using domain-specific, spreading activation methods, clinical free-text can be anonymized with higher accuracy. First, however, the adaptive machine learning systems are to be trained.

Machine Learning from Corpora

Natural language processing researchers often turn to the use of corpora, or bodies of text, to provide them with an understanding of the language structure and use. Although Chomsky, in 1968, argued against the use of corpora in linguistics on the grounds that the interesting questions about language were much too complex to be answerable from a small sample of the language, (see, e.g., Chomsky N. Language and Mind. New York: Harcourt Brace; 1968) development and use of corpora is routine to computational linguistics. There are a number of well-established corpora, such as: WordNet (a large database of English terms with semantic relations), Penn TreeBank (a large database of terms from various news stories, technical publication, and the Brown corpus), ACIP (Asian classical works), ACET (English, American and western literature), Moby (Shakespearean works), NCSTRL (computer science technical report library).

These corpora are from either a general language source or a conglomeration of general language sources. Unfortunately, because clinical-free text has a different structure than these sources, they are not viable for natural language processing research that involves clinical free-text. Currently there is only one known publicly available corpus of clinical free-text (we exclude corpora of edited biomedical literature because it lacks the free text aspect, and because of the previously mentioned likelihood of complex discourse goals such as argumentation). This corpus is the Cincinnati Unsupervised Pediatric Corpus. It contains 590,000 clinical tokens and part-of-speech tags. One reason for this absence of corpora is due to the confidentiality of medical data another is that organizations typically like to keep this valuable data for their own research. In our work we have created one additional annotated corpus, the Cincinnati Supervised Training Corpus, and annotated the Cincinnati Unsupervised Pediatric Corpus by validating the part-of-speech tags and including UMLS concepts. It is through this process that we also introduce novel machine learning methods.

These corpora are important. First, they may be useful for training and comparison of medical NLP systems. Second, even a small amount of medical corpora can have a large impact on part-of-speech (POS) tagging of medical texts as long as domain expertise is incorporated. See, e.g., Pakhomov S, Coden A, Chute C G. Developing a Corpus of Clinical Notes Manually Annotated for Part-of-Speech. International Journal of Medical Informatics. 2006; 75(6):418-429. The study of the Manchester tagger backs this up by demonstrating that there can be significant transfer of learning from one type of medical text to another. Learning the patterns of the Genia corpus helps with Pubmed abstracts in other domains. We expect to find the same thing in pediatric clinical free-text. See, e.g., Kim J-D, Tomoko O, Teteisi Y, Tsujii J. Genia Corpus—A Semantically Annotated Corpus for Bio-Textmining. Bioinformatics. 2003; 19 (suppl.)(1):190-182 and Tateishi Y, Tsugita A. Part-of-Speech Annotation of Biology Research Abstracts. Paper presented at: Proc. of Language Resources and Evaluation Conference, 2004; Paris, France.

Aspects of the Approach

Semantic networks and spreading activation have been used in 1) computational models of brain functions; 2) semantic networks to represent various features of semantic memory and; 3) associative search in information retrieval. These applications have been based on small-scale networks that were usually constructed manually as a knowledge-engineering exercise. See, e.g., Crestani F. Application of Spreading Activation Techniques in Information Retrieval. Artificial Intelligence Review. 1997; 11 (6):453-482. Applications of spreading activation networks in information retrieval either follow the links between documents, (see, e.g., Crestani F, Lee P L. Searching the Web by Constrained Spreading Activation. Information Processing and Management. 2000; 36(4):585-605.) or use some measure of statistical similarity between documents. Statistical approaches to natural language processing are based on word co-occurrences, trying to capture meaning in context windows. The following attributes are desirable but missing from previous approaches:

Recognizing the overall topic, weakly priming all concepts associated with a specific area (for example, one or more medical domains), and thus anticipating possible meanings.

Recognizing characteristic concepts that will strongly prime relevant network nodes, creating initial seed activations.

Using real knowledge to approximate semantic memory associations of an expert for spreading activations from already active concepts to related concepts.

Building consistent interpretations of the text analyzed (episode), by adding new concepts found in the text, expanding acronyms and abbreviations for those meanings that best fit the active sub-network thus, increasing the overall consistency of text interpretation.

Inhibiting competing interpretations to restrict spreading of activations using known constraints that increase overall consistency of interpretation, including active searching when ambiguities persist.

As a result, detailed annotation of texts, based on interpretation of the larger fragments rather than local context, can be realized.

Synopsis

A goal of the computer implemented systems and methods of this invention is to enhance the accuracy of clinical free-text mining by developing domain specific spreading activation methods that mimic human memory models.

Spreading activation is a neuro-cognitive model that attempts to simulate human memory by creating networks of information, called semantic networks. This fundamental neuron-cognitive process and related computational approach are rarely acknowledged in the natural language processing of clinical free-text. Yet, it is reasonable to propose that by involving some form of artificial memory, such as recognition, semantic and episodic, clinical free-text can be mined more effectively. It is hypothesized that reaching human level competence in understanding clinical and other free-texts calls for a neuro-cognitive approach that requires memory based models that rely upon, for example, a annotated pediatric corpus and that providing such a corpus will enable significant scientific advances in natural language processing.

Like other artificial intelligence methods, spreading activation relies on training corpora. Since annotation is costly, we attempt to heuristically bootstrap valid corpus annotations by initially annotating smaller corpora; then relying on technology to extend the latter into heuristically valid annotations of a much larger corpus. For these efforts two corpora are employed using anonymized data. Linguists and clinicians operating a careful system of quality control can create one corpus, the Cincinnati Pediatric Supervised Corpus (CPSC). Part-of-Speech (POS) quality can be monitored in formal reviews, and corrected as necessary. Unified Medical Language System (UMLS) concepts can be added to the Cincinnati Pediatric Unsupervised Corpus (CPUC). The CPUC is an existing corpus of 590,000 tokens that has been randomly selected from pediatric transcriptions, scrupulously anonymized and then semi-automatically annotated with POS labels. See, e.g., Pestian J P, Itert L, Meyer S. Development of the Cincinnati Pediatric Clinical Corpus. *International Journal of Biomedical Informatics*. 2006; Forthcoming.

Methods

The approach used here is to simulate semantic/episodic memory using ULMS knowledge (concept and relations) to create a Graph of Consistent Concepts (GCC) that represents text as an active part of semantic memory. GCC has a number of parameters that may be tuned by using an annotated corpus. This section describes the experimental process and methods that we use to test the hypothesis: Neurocognitive methods, such as spreading activation (represented by a GCC), trained on an annotated pediatric corpus may have greater accuracy than alternative methods.

Annotation Process

Annotating the Cincinnati Supervised Training Corpus

The initial step is to develop the CSTC, a domain specific supervised training corpus. This can be done by randomly selecting 30-50 clinical free-text reports from pediatric radiology, nephrology, pulmonary, behavioral medicine, psychiatry, rheumatology, pathology, cardiology, allergy and immunology, critical care, hematology/oncology, and human genetics. Our encryption broker will anonymize and normalize much of the free text, (see, e.g., Pestian J P, Itert L, Andersen C L, Duch W. Preparing Clinical Text for Use in Biomedical Research. Journal of Database Management. 2005; 17(2):1-12.) our ontologizer (see FIG. 4) will assign UMLS concepts to these data. The text will then be presented to clinical experts to disambiguate any ambiguous concepts via the Ontologizer software. Our clinical experts will review the assigned concepts. If a concept is ambiguous, the expert will select the appropriate concept from the list of provided concepts. FIG. 4 shows the concept disambiguation interface. Concepts may be color-coded. For example, the identified concepts that have been disambiguated in this session may be colored green. Concepts in blue may have been disambiguated in previous sessions. Yellow concepts may need to be disambiguated during this session. In an exemplary embodiment, the concept colored red may be the one that is currently being disambiguated. A list of options 208 from the UMLS for the red token is listed below the text 206. The software may also provide inter-rater consistency and reliability reports. For example, a report of consistency between raters can be printed. If the raters were not consistent, the classifications may be discussed between the raters until agreement is made. Upon completion of this process, supervised corpora with expert classification will be developed.

Annotating the Cincinnati Unsupervised Training Corpus

Figure 5:
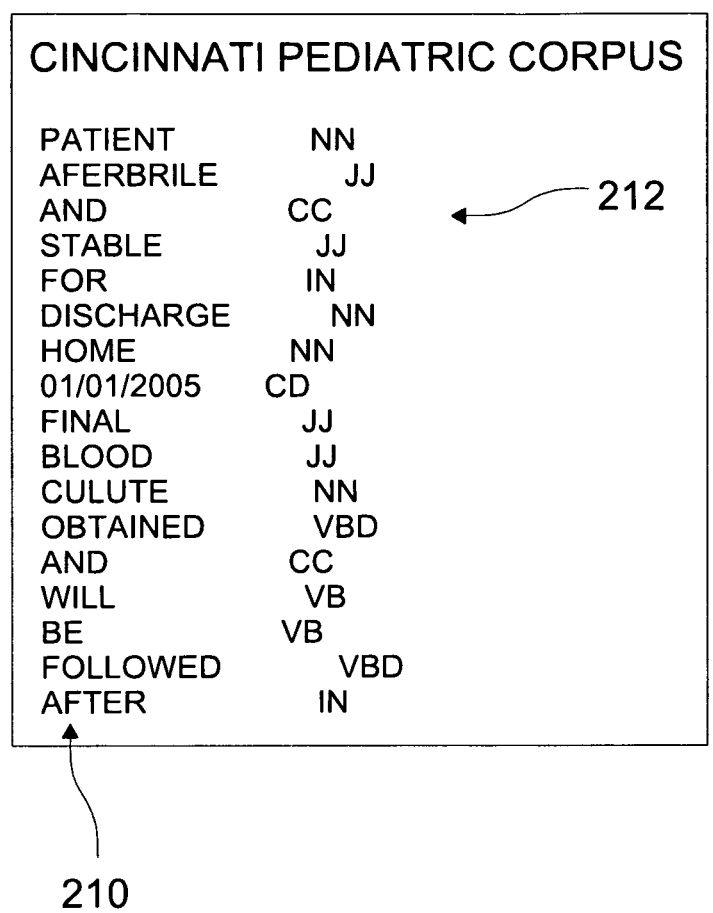
FIG. 5 depicts a sample of an exemplary corpus that has been parsed and cleansed for acronym, jargons, names, and dates.

Currently, the CUTC contains individual tokens 210 and a hand annotated POS 212. A sample is shown in FIG. 5. The sample shows the text after it was parsed and cleansed for acronyms, jargons, names, and dates. For example, in the original text, the last token 210 (before the ".") listed was changed from "d/c" to "discharge". Each token 210 has also been tagged with the appropriate part of speech 212 using the Penn Treebank tagset. In this tagset, NN is a singular noun, JJ is an adjective, CC is a coordinating conjunction, IN is a preposition, CD is a cardinal number, and VBD is a past-tense verb. When the CUTC was developed, the quality of the POS tags was not established. Using the methods described in the Quality Assessment section, the POS tags of the CUTC can be evaluated.

The procedure for measuring the quality of the CUPC is described below. Samples of the corpus, however, will need to be created. Sentences from the CUTC are randomly selected until there are at least 5,000 tokens. These tokens can then be retagged by hand. This tagging process includes triple checks of accuracy. That is, three different people will tag an untagged 5,000-token corpus with the Penn Treebank tag set. Their tags will then be compared for internal consistency. If an item is inconsistent, a senior linguist will review it, and the tags will be made consistent. This initial training set will be put in the format required by TreeTagger or the most appropriate POS tagger at that time. The POS tagger will be trained using the sample of 5,000 tokens. The trained POS tagger will then be used to annotate the entire CUTC.

Measuring Annotation Quality

There are two types of evaluation: evaluating the quality of hand tagging of the CSTP, and evaluation of the machine-based tagging. The second evaluation is not the same as evaluating the spreading activation method against other information retrieval methods; rather, it is an evaluation of the quality of the corpora being developed. Evaluating the spreading activation method is discussed below.

The kappa coefficient and its possible variants may be used to evaluate machine-based annotation with the hand tagged POS, or POS tagging between two hand-taggers. The kappa coefficient provides an estimate of the proportion of agreement above chance. Kappa index is often used in diagnostic procedures when different binary response variable (Presence/absence) are used on a large number of subjects/patients, and each patient is "rated" by two or more diagnostic procedures or clinicians. When the classification procedure of interest, such as the present annotation (concepts) issue, has multiple nominal categories (tags), assessment of agreement becomes somewhat more involved.

There may be a machine-based procedure and one manual procedure or two manual tagging procedures. Each token of clinical free-text may be assigned one of possibly 40 or more different types of tags (from Penn TreeBank) for each procedure. The tagging process by any of the two methods (be it two manual taggers or one manual and one machine-based, or both machine-based—one with spreading activation and the other without) may be summarized as an R×R square contingency table, where $x_{ij}$ denotes the number of tokens that are tagged as "i" by one procedure, e.g., manual, and as "j" by another, e.g., machine, procedure, i=1, 2, ..., R, j=1, 2, ..., R. R is the total number of possible tags. A tag-specific measure of agreement may be obtained to examine the extent to which the two processes tend to lead to consistent conclusions with respect to the particular tag.

In this process there is an implicit assumption that the particular nature of any disagreements are not of interest. The R×R table will be collapsed to a 2×2 table constructed by cross-classifying tokens with binary indicators such that a particular POS (say NN) is tagged by both procedures or not. A tag-specific kappa statistic may be obtained for each tag providing, as many kappa statistics as there are tags. In addition, an overall summary index of agreement will also be obtained. The composite measure of agreement across all the tags (an over all kappa) may be obtained as a weighted average of individual kappa values, where the weights are denominators of the individual kappa values. Statistical Analysis System (SAS) may be used to compute all indices. Although there may be "high-dimension" contingency tables with large number of cells with 0 or sparse cell frequencies, SAS is well equipped for obtaining exact Kappa statistics in these conditions.

There is a theoretical upper limit of each Kappa that is a function of the marginal frequencies (i.e., the prevalence of various tags for the entire set of tokens in the annotated text). In particular, the estimate of kappa can take a maximum value of 1 only when the marginal frequencies are exactly equal and all off-diagonal cells are zero. Once the kappa statistic is computed, it will also be represented in descriptive terms. Landis and Koch provide ranges that suggest, beyond what one would expect by chance, Kappa>0.75, typically representing excellent agreement, 0.40<Kappa<0.75, fair to good agreement, and kappa<0.40 as poor agreement. See, e.g., Landis J R, Koch G G. The Measurement of Observer Agreement for Categorical Data. Biometrics. 1977; 33(159-174). While there is some appeal to this convenient framework, caution should be used when accepting the results, particularly in view of the large number of tags and the dependence of kappa on marginal frequency of various tags in the sample. Once the investigators have approved the quality, the completed CSTC may then be used to train a spreading activation model that may applies UMLS concepts to the CUTC.

Concept Mapping Using Spreading Activation and Competing Models

The concept mapping research is divided into four sections: assignment of UMLS identifiers, full concept identification, concept weighting computation, and decay function computation.

Assignment of UMLS Identifiers

In this phase, 50% of the annotated CUTC may be used to train the spreading activation software described above. After the training is complete, the software may be used on the other half of the CUTC to determine the appropriate CUI, Every Word Identifier (EUI), and Word Unique Identifier (WUI) found in the UMLS. The training and test parts may then be reversed and the procedure repeated (two-fold cross-validation procedure).

Figure 6:
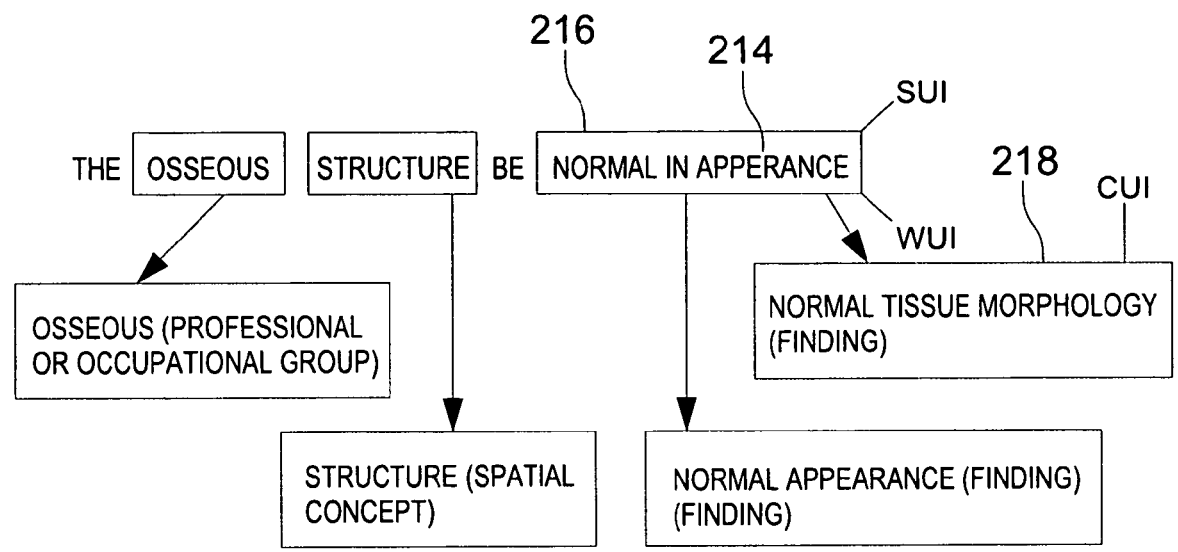
FIG. 6 depicts an exemplary simplified schema for mapping text to concepts.

FIG. 6 presents a simplified schema for mapping text to concepts. In this case the token appearance 214 is assigned to a WUI found in the UMLS (note the WUI connection line terminates at the token). The phrase normal in appearance 216 is assigned to a SUI found in the UMLS (note in the figure the SUI connection line terminates at the phrase box boundary). This phrase has an established concept in the UMLS entitled normal tissue morphology (Finding) 218. Every word (EUI) in the text is mapped to its normalized form (WUI). Unique string identifiers (SUI) are composed for the WUI.

Concept Identification and Mapping

To map phrases (SUI) to concepts (CUI) the following algorithm can be used on each token:
a) Using the trained POS tagger, assign POS tags to every token.
b) Map all the words to their normalized forms.
c) Scan normalized words from the end of the text.
  a. If a POS tag matches one of the symbols:
    i. Cardinal Number (CD), adverb (RB), adjective or numeral, ordinal (JJ), Noun (NN), Verb (VB), Listed item marker (LS), Symbol (SYM), start scanning the text from the current position towards the beginning of the text. Add words to a phrase that match mentioned POS tags until there is a phrase that is not in the UMLS
    ii. 3b. Resume after the position where the last UMLS phrase was found.
d) Finish when at the beginning of the text.

The paragraphs below show a test of this approach using a radiological (ultrasonography) transcription that was mapped to a concept space, using the algorithm described above that was built into the software. The second paragraph shows the identified concepts in bold.

Original Text: "Fever, left flank pain, pyelonephritis. The right kidney is normal in sonographic appearance with no evidence of scarring, hydronephrosis or calculi. It measures XXXX cm, which is normal for patient's age. The left kidney is enlarged. It measures XXXX cm in length. No focal areas of abnormal echogenicity or scarring are seen. No hydronephrosis or calculi are identified. Images of the bladder demonstrate no abnormality. Enlargement of the left kidney, which may suggest acute pyelonephritis. This could also represent a normal variant. Normal appearing right kidney."

Normalized and UMLS Concept Identified Text: "fever, left flank pain, pyelonephritis. the right kidney be normal in sonographic appearance with no evidence of scar, hydronephrosis or calculus. it measure xxxx cm, which be normal for patient's age. the left kidney be enlarge. it measures xxxx cm in length. no focal area of abnormal echogenicity or scar be see. no hydronephrosis or calculus be identify. image of the bladder demonstrate no abnormality. enlargement of the left kidney, which may suggest acute pyelonephritis. this can also represent a normal variant. normal appear right kidney."

Concept Weighting

The next phase is to weight the SUIs and CUIs. To do so, the relational file, MRREL.RRF, contained in the UMLS (edition 2005AB) may be used. This file contains 5,499,792 unique relationships between EUIs in a matrix form. The CUI concepts linked by these relations form a huge semantic network, but only a small sub-network is important to analyze a given text. A weight linking pair of concepts (two nodes in the graph) is computed using relational matrix entries. The weights are defined as conditional probabilities:

$$w_{ij}=P(j|i)=C(CUI_i,CUI_j)/N(CUI_i)$$

where:
W={$w_{ij}$} weight matrix with weights between i-th and j-th concept CUI, C($CUI_i$, $CUI_j$) is the number of co-occurrences of $CUI_i$ and $CUI_j$ concepts in the relational table row, and
N($CUI_j$) is the number of occurrences of a $CUI_i$ concept in the relational table.

Weights between concepts resulting from mutually exclusive interpretations of phrases or acronyms should be negative, leading to inhibition of some concepts. For example, CCU may be expanded as "Cancer Care Unit" or "Coronary Care Units", but if some strongly active nodes related to heart, cardiology or similar concepts are already present the second concept will be preferred and spreading of activation should inhibit the first concept; to achieve this strong inhibitory response, links between the preferred concept should be present. These links should be added between all distinct concepts that are proposed as candidates. The National Library of Medicine's MetaMap software may assist in this stage.

Decay Function

All well-defined and unambiguous concepts are used to activate the graph nodes as a first step to create a graph of consistent concepts (GCC) (see FIG. 3). Activation then spreads from active node to active node. Calculating the activation weights of these nodes is done using Equation 1. Connections are non-symmetric, and two active nodes may strengthen their activity, thus mutually activating each other. To make sure the spreading does not occur over the entire network a constraint must be applied. As noted earlier, the distance, the fan-out, and the path activation constraint have been traditionally employed to constrain activation. Except for inhibition, a decay function will be introduced as a novel method for slowing activation spread over the network. This method includes the concept of time, something not used in the other constraints. In this type of constraint activation potential can be spread according to W matrix as the activation potential α

Equation 4. Decay Function $$\alpha^{(t+1)}=w_{ij}H(\alpha(t))+\alpha(t)$$

where:
$w_{ij}$=the weight of cell ij in matrix W
H is either a step function or sigmoidal function (Equation 3), (see, e.g., Rocha C, Schwage D, Poggi Aragao M. A Hybrid Approach for Searching in the Semantic Web. Paper presented at: International World Wide Web Conference, 2004; New York, N.Y.) and
t=time, also referred to as iteration number.
α<1=is a decaying parameter Using this decay function a can determine if the next pulse should occur down a particular path, or that path is ignored. The UMLS, though big, is a very general knowledge base and lacks the specific weights that would be available with expert knowledge or that could be learned from annotated corpus.

In an exemplary study, two small radiology corpora were created. Each corpus had 30 chest x-ray transcriptions, for six different diseases. An assumption was made that the most consistent concepts would have the highest activation. The initial unsupervised weights were able to give maximum activation of only 79% of the correct concepts. A radiologist then reviewed the text and disambiguated any ambiguous concepts using the ontologizer software shown in FIG. 4. This supervised training set was then used to train the spreading activation software for identifying concepts in similar radiology transcriptions. By manually adding correct relationships, correct concept identification increased to 96%. FIG. 7 compares these results. It shows that the second corpus is much more semantically complicated and harder to learn.

Accuracy with and without Training.

Enriching UMLS relations means adding N(CUIi) and C(CUIi, CUIj) for all pairs of concepts from an annotated text. To check the usefulness of the project, an accuracy measure that focuses only on the ambiguous mappings was used. If the maximally activated CUI corresponds to a manually chosen CUI, a point was added. Overall, Corpus I had 140 ambiguous phrases and Corpus II had 301 phrases.

Evaluation

Several aspects of the proposed design may be evaluated. Firstly, the mere act of training on clinical free-text may improve performance on part of speech tagging. Here there is no option but to create a small gold-standard corpus, evaluate inter-rater reliability of the tagging task then use the tagger to construct the kind of analysis that is found in Tsuruoka et. al. For example, Tsuruoka's part-of-speech tagger is specifically suitable for biomedical text. It was built based on the cyclic dependency network with maximum entropy modeling with inequality constraints. See, e.g., Toutsanova K, Klein D, Manning C D, Singer Y. Part-of-Speech Tagging With a Cyclic Dependency Network. Paper presented at: HLT-NAACL, 2003. It was evaluated on three corpora: the Wall Street Journal corpus, the GENIA corpus, and the PennBiolE corpus. Results indicated that adding data from different domains did not hurt the performance of the POS tagger and the POS tagger had very good performance (97% to 98%). See, e.g., Tsuruoka Y, Tateishi Y, Kim J-D, et al. Developing a Robust Part-of-Speech Tagger for Biomedical Text. Paper presented at: Advances in Informatics-10th Panhellenic Conference on Informatics, 2005; Volos, Greece. It was, however, not tested with pediatric or any clinical free-text. Since we are using the Penn Treebank tagset we have the luxury of using the results of Tsuruoka et. al., for comparison. We may achieve results better than the preliminary results that Tsuruoka et. al, report for phrase chunking, because we make use of information about the presence or absence of a phrase in UMLS, while they do not.

Secondly, holistic processing of the text using spreading activation may produce good disambiguation decisions. A relevant comparison here is n-gram based WSD technology, as used by Pedersen and Lapata and Brew, 2004. See, e.g., Pedersen T. An Ensemble Approach to Corpus Based Word Sense Disambiguation. Paper presented at: Proceedings of the Conference on Intelligent Text Processing and Computational Linguistics, 2000; Mexico City and Lapata M, Brew C. Verb Class Disambiguation Using Informative Priors. Computational Linguistics. 2004; 30(1):45-73. If augmented with a simple implementation of the one-sense-per-discourse heuristic, this will provide an inexpensive but reasonably well-informed baseline against which to compare the spreading activation technology. Standard evaluation techniques for word-sense disambiguation apply. There are some technical difficulties that will arise because prior errors in phrase chunking may prevent the disambiguation component from even seeing some of the candidates that should have been identified and disambiguated. In this case we will quote precision and recall figures both for the system as a whole and for the individual components, in the latter case taking account of the fact that the disambiguation component should not be blamed for the failings of the segmenter.

Thirdly, spreading activation may make those things similar that ought to be similar and those different that ought to be different. Since spreading activation induces a similarity structure between the nodes of the graph, it may be possible to use it to average over the whole corpus and obtain affinity scores. See, e.g., Brew C, Walde S S. Spectral Clustering for German Verbs. Paper presented at: Conference on Empirical Methods in Natural Language Processing, 2002; Philadelphia, Pa. This evaluation treats spreading activation as a whole-corpus clustering procedure, and can be evaluated in the same way as either standard or spectral clustering methods.

Example Data Set

One way to illustrate an example data set is to compare how a medical records professional would determine a radiology billing and how an embodiment of the present invention does it. Assume that the patient discharge report includes the following statement:

This patient had a history of left ureteral stone. Small renal calculus in the renal pelvis cause mild left hydronephrosis. Possible intrarenal left stone is also noted.

The medical records professional would start by recognizing that the information is related to renal disorders. Then, key concepts are identified. Here they are italicized.

This patient had a history of *left ureteral stone*. *Small renal calculus in the renal pelvis* cause mild left *hydronephrosis*. *Possible intrarenal left stone* is also noted.

After this, the medical records professional weights the information in his/her mind and assigns a billing code.

Now, when an embodiment of the present invention processes the same statement, it will first normalize the text. Next, it will identify medical concepts in the normalized text (the medical concepts shown italicized in the normalized text below):

this patient have a history of *left ureteral stone*. *small renal calculus in the renal pelvis* cause mild left *hydronephrosis* possible *intrarenal left stone* be also noted.

Figure 8:
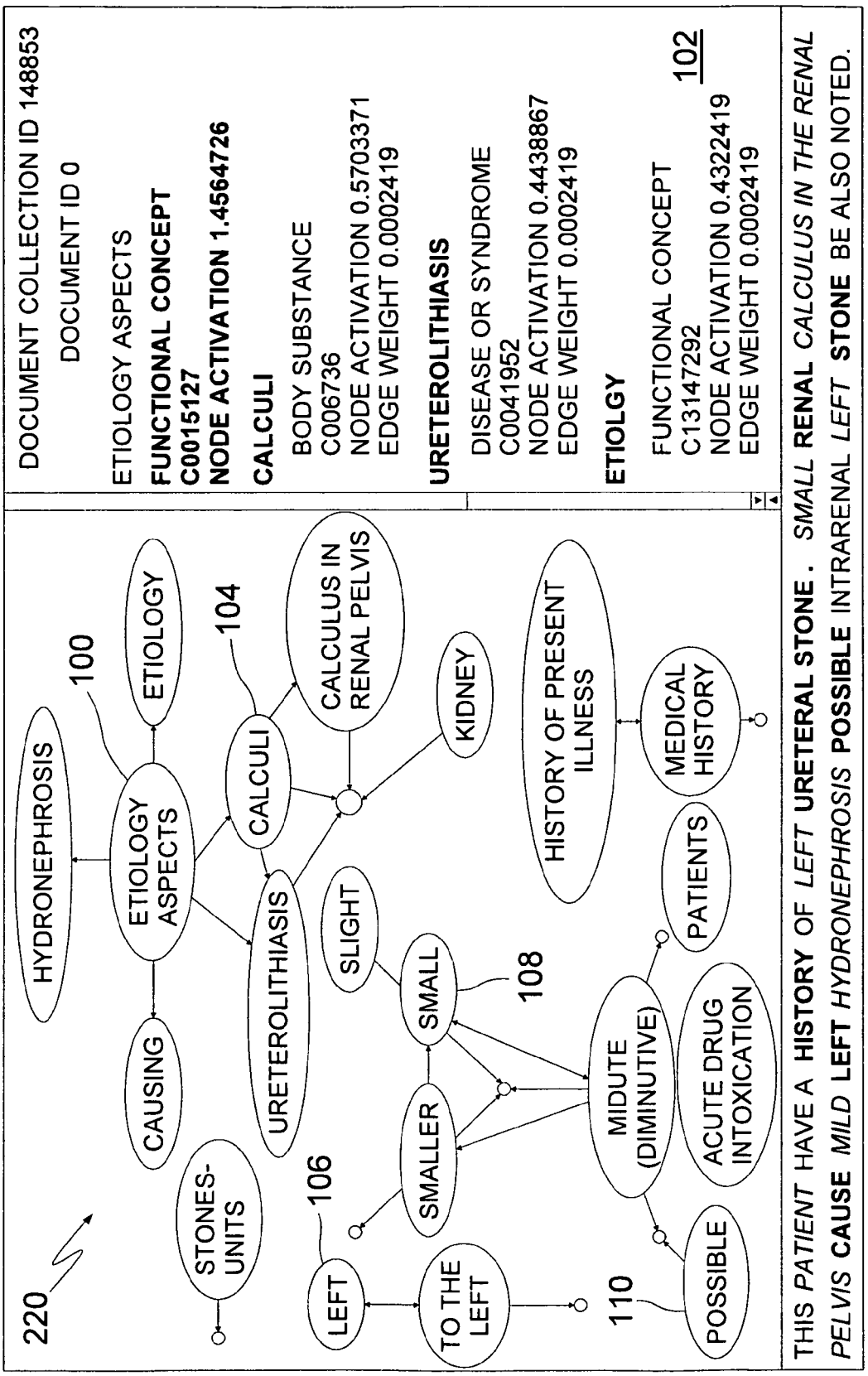
FIG. 8 is a graph of consistent concepts generated by an exemplary embodiment of the present invention.

Next, as shown in FIG. 8, a semantic network 220 is formed and weights are assigned. FIG. 8 is a graph of consistent concepts generated by an exemplary embodiment of the invention. When the oval "Etiology Aspects" 100 is selected, the column on the right 102 lists the possible sources and weights associated with etiology. Here "calculi" 104 had the heaviest weight. Other nodes show that "left" 106, "small" 108 and "possible" 110 cluster together. From this network the item with the heaviest weight is selected and a billing code that has already been integrated into the ontology is assigned. If the a billing code is not yet associated with the item having the heaviest weight, a Health Information Management professional may be queried by the system to curate the data and manually assign a billing code. The system may learn from the HIM professional and it may remember the correct coding result thereby expanding its knowledge base. Finally, the entire cycle is repeated for each new patient visit.

While the example dataset is used in the process of assigning a billing code for a medical facility, it will be appreciated that the invention can be used for many medical and non-medical purposes. For example, and without limitation, the invention can be used for mining large information sources (legal discovery materials, for example), analyzing suicide notes, and for creating an artificial expert which may be useful, for example, to enhance delivery of personalized medical care.

Neurocognitive computing is germane to legal research in that it can provide a semantic network of past knowledge and use that network to find relationships in current knowledge. For example, during the discovery stage it may find that Joe Smith could not be responsible for hit-and-run because he was receiving a speeding ticket at the time of the hit-and-run. The methods enable the discovered information to be linked using natural language processing methods like spreading activation.

In another application, embodiments of the invention may be used to analyze suicide notes. Suicide notes and recorded discussions with suicidal patients are artifacts of the patient's inimical thoughts. These patients are generally experiencing some level of psychache. Psychache refers to the hurt, anguish, soreness, aching, psychological pain in the psyche. See, e.g., Shneidman E S. Suicide as psychache. J Nerv Ment Dis. 1993; 181:145-147. Psychache perturbs the mind to a point where suicide becomes an escape from this pain. See, e.g., Shneidman Edwin. How I read. Suicide Life Threat Behav. 2005; 35:117-120.

In all age groups suicide notes are left behind between 15% and 43% of time, but there is evidence that the higher percentage is skewed by age. See, e.g., O'Donnell I., Farmer R., Catalan J. Suicide Notes British Journal of Psychiatry. 1993; 163:45-48; Salib E, El-Nimr G, Yacoub M. Their last words: a review of suicide notes in the elderly. Med Sci Law. 2002; 42:334-338; and Salib E, Cawley S, Healy R. The significance of suicide notes in the elderly. Aging Ment Health. 2002; 6:186-190. What is in a suicide note? Menniger suggested that "the wish to dies, the wish to kill and the wish to be killed must be present for suicide to occur", (see, e.g., Menninger K. Man against himself. Harcourt Brace 1938) but there is a paucity of research exploring the presence of these motives in suicide notes. Brevard, Lester and Yang analyzed notes to see if Menniger's concepts were present. Without controlling for gender, they reported more evidence for the wish to be killed in suicide notes of completors than the notes of non-completors. See, e.g., Brevard A, Lester D, Yang B. A comparison of suicide notes written by suicide completers and suicide attempters Crisis. 1990; 11:7-11. Laaneers, et al revisited Menninger's triad and compared 22 suicide to 22 parasuicide notes that were carefully matched. They concluded that the notes from completors were more likely to have content reflecting anger or revenge, less likely to have escape as a motive, and, although it was not statistically significant, there was a tendency to show self-blame or self-punishment. In another study of 224 suicide notes from 154 subjects, note-leavers were characterized as young females, of non-widowed marital status, with no history of previous suicide attempts, no previous psychiatric illness, and with religious beliefs. Suicide notes written by young people were longer, rich in emotions, and often begging for forgiveness. Another study noted that statements found significantly more frequently in genuine notes included the experience of adult trauma, expressions of ambivalence; feelings of love, hate and helplessness, constricted perceptions, or loss and self-punishment. One important and consistent finding is the need to control for differences in age and gender. See, e.g., Leenaars A. A., Lester D., Wenckstern S., Rudzinski D., Breward A. A comparison of suicide notes written by suicide notes and parasuicide notes Death Studies. 1992; 16.

Determining the likelihood of a repeated attempt by ideators and attempters is an important role of a medical facility's psychiatric intake unit and notoriously difficult because of a patient's denial, intent for secondary gain, ambivalence, memory gaps, and impulsivity. See. e.g., Freedenthal Stacey. Challenges in assessing intent to die: can suicide attempters be trusted? Omega (Westport). 2007; 55:57-70. One indicator of the severity and intent is simply the presence of a suicide note. Analysis has shown that patients presenting at an emergency department with non-fatal self-harm and a suicide note suggests that these patients were likely to be at increased risk for completing suicide at a later date. See, e.g., Barr Wally, Leitner Maria, Thomas Joan. Self-harm or attempted suicide? Do suicide notes help us decide the level of intent in those who survive? Accid Emerg Nurs. 2007; 15:122-127. Evidence of a suicide note, may illuminate true intentions but, the lack of one does not squelch questions. For example, without a note is the patient substantially really less severe, or how many patients committed suicide without leaving a note behind? Is there a difference between the notes of completors and attempters? Valente's matched notes from 25 completors and attempters found differences in thematic content like fear, hopelessness and distress. On the other hand, Leenaar's found no significant difference between thematic groups. See, e.g., Valente Sharon M. Comparison of suicide attempters and completers. Med Law. 2004; 23:693-714 and Leenaars A. A., Lester D., Wenckstern S., Rudzinski D., Breward A. A comparison of suicide notes written by suicide notes and parasuicide notes Death Studies. 1992; 16. These studies, however, were unable to take advantage of current NLP and machine learning (artificial intelligence) knowledge. Recently, Handleman incorporated basic NLP methods like word-counts and a rough approximation of a semantic relationship between a specific word and a concept. For example the concept of time was semantically represented by the words day or hour. The univariate analysis using just word count found no difference between notes. When gender was controlled, some semantics differences like: positive emotions, time, religion, and social references emerge. See, e.g., Handelman Lori D, Lester David. The content of suicide notes from attempters and completers. Crisis. 2007; 28:102-104.

The NLP methods described herein are directly applicable to the analysis of suicide notes because they are the basis of a generalizable method for classification and text mining. In an initial experiment we constructed a corpus of 66 suicide notes written between 1945 and 1953 of which 33 are completors and 33 are simulated notes. See, e.g., Shneidman E S, Farberow N L. Clues to Suicide. McGraw Hill Paperbacks 1957. There is no analog to the UMLS for suicide notes, so we used individual words to create a feature space. This yielded a 66 rows×922 columns matrix. Decision trees were chosen for the classification task. We tested the C4.5, CART, and Random Forest algorithms. Preliminary classification of texts revealed that words alone are good simulated/completor predictors. The results showed that approximately 93% of the notes could be classified appropriately. See, e.g., Pestian J. P., Matykiewicz P. Comparison of machine learning algorithms: Distinguishing between real and simulated suicide notes. Submitted to AMIA Spring Conference 2008. Accordingly, exemplary embodiments of the present invention may be used to analyze suicide notes. Such analysis may assist a clinician in assessing the risk that an individual may attempt suicide in the future.

Personalized Medicine is the delivery of health care that is based upon an individual's specific genotype, current clinical state and environmental conditions. Optimal personalized medicine decisions require caregivers and case managers to have access to data not only about the individual but also about the background medical knowledge that should underpin individualized decisions. Embodiments of the invention pertaining to Personalized Medicine are adapted to deliver essential, relevant medical information to caregivers for consideration when planning a patient's personalized medical treatment. For example, artificial experts may be utilized to assist in choosing appropriate drugs and dosages for certain diseases or conditions, such as attention deficit hyperactivity disorder, autism, depression, and epilepsy.

In an embodiment, each document $D_i$, i=1 ... N(t) is represented by a row of j=1 ... n(t) binary features; therefore the whole vector representation of all documents in iteration t is given by a matrix D(t) with N(t)×n(t) dimensions. The dimensions vary as new query terms are found. UMLS contains relations $R_{ij}$ between concepts i and j. Selecting only those concepts i that have been used as features to create matrix D(t) and those concepts j that are related to i and representing the existence of each relation as a Kronecker $\delta_{ij}$, a binary matrix R(t) is created. Multiplying the two matrices D(t)R(t)=D'(t) gives an expanded matrix D'(t) with new columns defining enhanced feature space. These columns contain integer values indicating the document with which the new concept is associated. For class k=1 ... K a binary vector $C_{ki}=\delta_{ij}$, i=1 ... N(t) serves as a class indicator of all documents. To evaluate the usefulness of the candidate features the Pearson correlation coefficients between these columns and all vectors that are class indicators are calculated. Only those candidate features with high correlation coefficients are retained. After removal of some matrix columns and binarization of the remaining ones, D'(t) is converted to a new current matrix D(t+1).

Using spreading activation networks that are tuned with domain expertise, machine-attempts to retrieve information should reach results close to, or better than, human levels. Unfortunately ULMS is not an encyclopedia of medical knowledge and does not contain all associations of an expert. Enriching UMLS relations by a supervised training procedure may be done by updating the C(CUIi, CUIj) matrix for all pairs of concepts from an annotated corpus. One active search algorithm to uncover new relations has been described recently. See, e.g., Szymanski J, Sarnotowicz T, Duch W. Towards Avatars with Artificial Minds: Role of Semantic Memory. Ubiquitous Computing and Intelligence, American Scientific Publishers. 2006; In Press. In essence it may use the ULMS semantic types and ontology to search for relations between subsets of concepts that belong to two semantic types (for example, "disease or syndrome" and "sign or symptom", in medical textbooks and other trustworthy information sources.

Figure 9:
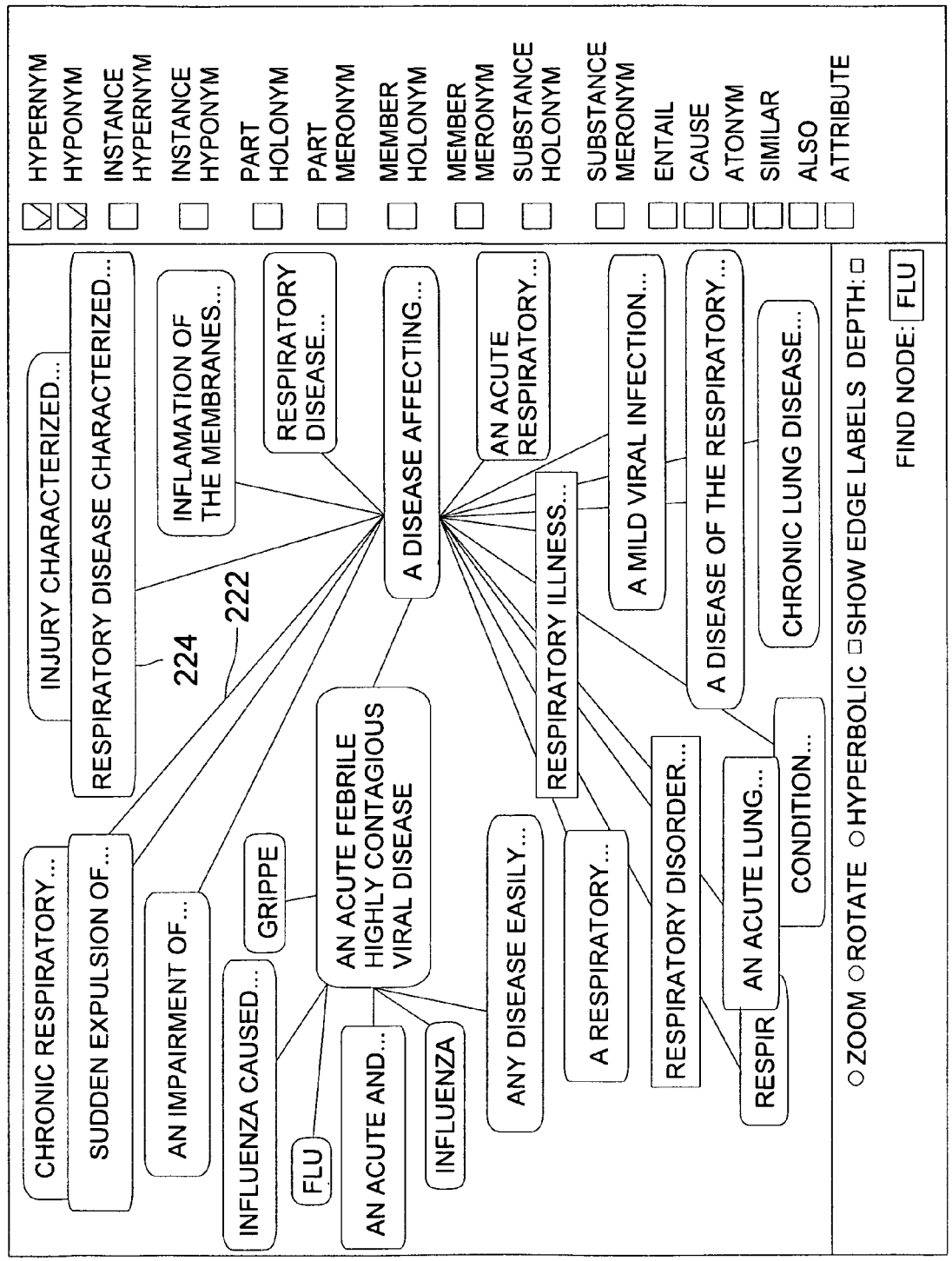
FIG. 9 is a screen capture of an exemplary computer-based graphics tool, operating on an exemplary computerized system according to the exemplary embodiments, for manually correcting the relations between concepts according to the present invention.

A graphics tool has been created to facilitate manual corrections to the relations 222 between concepts 224 (FIG. 9). This tool builds upon software for creating GCC's. The graphics tool may also be converted to explore the ULMS concepts and relations. This tool can greatly simplify adding links between concepts or removing wrong ones and improving the knowledge base for semantic memory.

The present invention provides a computerized system and method for performing natural language processing of free text using domain-specific spreading activation. While the invention would typically be hosted by a server connected to the Internet, the concept can include other types of networks, such as local area networks (LANs), wide area networks (WANs), and public data networks, by which client workstations obtain data from a server workstation.

Each workstation may comprise a microcomputer such as a personal computer, for example, including a system bus that is connected to a central processing unit (CPU) and to memory, including read only memory (ROM) and random access memory (RAM). The system bus can be connected, via appropriate interfaces known to persons skilled in the art, to various input/output devices, including additional nonvolatile data storage devices, video and audio adapters, keyboard, mouse, and other devices that provide input to the workstation or receive output from the workstation. The workstation can also include a data port for communicating with other constituents of a collaborative data processing environment. The data port may be a serial port for linking the workstation to a modem or a communications adapter for connecting the workstation to a LAN.

Each workstation also typically includes software programs that are stored on the data storage devices or retrieved from other parts of a data processing system and loaded into RAM and then into the CPU for execution. Among those programs is a client program that receives messages from, and transmits messages to, other workstations connected to the network.

It is also within the scope of the invention that the software and associated data stores be located and operational on a stand-alone computer system, or any other type of computerized system as known to those of ordinary skill.

While exemplary embodiments of the invention have been set forth above for the purpose of disclosure, modifications of the disclosed embodiments of the invention as well as other embodiments thereof may occur to those skilled in the art. Accordingly, it is to be understood that the inventions contained herein are not limited to the above precise embodiments and that changes may be made without departing from the scope of the invention as defined by the claims. Likewise, it is to be understood that the invention is defined by the claims and it is not necessary to meet any or all of the stated advantages or objects of the invention disclosed herein to fall within the scope of the claims, since inherent and/or unforeseen advantages of the present invention may exist even though they may not have been explicitly discussed herein. All references cited herein are incorporated by reference.

What is claimed is:

1. One or more non-transitory electronic memory devices including computer instructions for performing a method for processing natural language, the computer instructions being configured to perform the steps of:
    providing access to a clinical text, the clinical text including a plurality of groups of characters;
    providing access to a first database and a second database, the first database including associations between a plurality of known words and a plurality of semantic concepts, and the second database including associations between a plurality of episodic concepts and at least one of the plurality of known words and the plurality of semantic concepts, the plurality of episodic concepts being separate from the plurality of semantic concepts;
    identifying one or more of the plurality of groups of characters as corresponding to at least one of the plurality of known words;
    creating a list of the identified known words;
    querying the first database to obtain a set of one or more semantic concepts associated with each of the identified known words;
    annotating the list of identified known words with the set of semantic concepts associated with each identified known word;
    querying the second database to obtain a set of one or more episodic concepts associated with the set of semantic concepts;
    creating a semantic network having a plurality of nodes corresponding to the sets of semantic and episodic concepts and weighted links between the sets of semantic and episodic concepts;
    utilizing spreading activation algorithms to refine the weighted links in the semantic network; and
    selecting at least one of the concepts from the sets of semantic and episodic concepts based upon an associated weight for the at least one node derived from the step of utilizing spreading activation.

2. The one or more non-transitory memory devices of claim 1, wherein the computer instructions are further configured to perform the step of preparing the clinical text prior to the identifying step, the step of preparing the clinical text including at least one of tagging parts of speech, replacing abbreviations with words, and correcting misspelled words.

3. The one or more non-transitory memory devices of claim 1, wherein the computer instructions are further configured to perform the step of providing an output including the selected at least one of the concepts.

4. The one or more non-transitory memory devices of claim 1, wherein the clinical text comprises clinical free text.

5. The one or more non-transitory memory devices of claim 4, wherein the clinical free text comprises pediatric clinical free text.

6. The one or more non-transitory memory devices of claim 1, wherein the clinical text comprises a plurality of documents and the computer instructions are further configured to perform the step of identifying a subset of the plurality of documents by identifying at least two documents having associations with the selected at least one of the concepts.

7. The one or more non-transitory memory devices of claim 6, wherein the computer instructions are further configured to perform the step of producing an output, the output including identification of one or more portions of each of the at least two documents having associations with the selected at least one of the concepts.

8. The one or more non-transitory memory devices of claim 1, wherein the clinical text comprises at least one suicide note and the method further comprises the step of evaluating the suicide note for concepts indicative of suicidal intent.

9. One or more non-transitory electronic memory devices including computer instructions for performing a method for processing natural language, the computer instructions being configured to perform the steps of:
    providing access to a clinical text containing natural language;
    tagging parts of speech in the clinical text;
    recognizing known words in the clinical text;
    creating a semantic network, the semantic network including at least one of the recognized known words and at least one relationship with at least one semantic concept associated with at least one of the recognized known words; and
    supplementing the semantic network by iteratively adding additional concepts and additional relationships to the semantic network until a termination requirement is met, each additional concept being associated with at least a prior one of the concepts and additional concepts in the semantic network by a respective additional relationship, at least one of the additional concepts being an episodic concept separate from the at least one semantic concept.

10. The one or more non-transitory memory devices of claim 9, wherein the computer instructions are further configured to perform the steps of
    weighting each of the at least one relationships and each of the additional relationships with a weighting value reflecting the strength of each relationship and additional relationship;
    determining a minimum threshold weighting value; and
    terminating the iterative growth of any network node in which the weighting between the relationships and the additional relationships do not satisfy the minimum threshold weighting value.

11. The one or more non-transitory memory devices of claim 10, wherein the computer instructions are further configured to perform the steps of
comparing the at least one semantic concept and the additional concepts to a list of known relevant concepts to generate a list of identified relevant concepts; and
providing an output based on at least one of a number and a significance of the identified relevant concepts.

12. The one or more non-transitory memory devices of claim 11, wherein the output pertains to a probability of a particular occurrence.

13. The one or more non-transitory memory devices of claim 12, wherein the clinical text includes at least one suicide note and the particular occurrence is a suicide attempt.

14. The one or more non-transitory memory devices of claim 10, wherein the clinical text includes a plurality of documents and the computer instructions are further configured to perform the steps of
receiving a query including a search concept; and
displaying a list of documents including one or more of the plurality of documents that is associated with the at least one semantic concept and the additional concepts that matches the search concept.

15. The one or more non-transitory memory devices of claim 14, wherein the list of documents is sorted by the weighting value pertaining to at least one relationship or additional relationship between the search concept and the corresponding recognized known word.

16. The one or more non-transitory memory devices of claim 9, wherein the one or more episodic concepts are uniquely associated with a patient's prior clinical history.

17. One or more non-transitory electronic memory devices including computer instructions for performing a method for processing natural language, the computer instructions being configured to perform the steps of:
providing access to a clinical text, the clinical text including a plurality of groups of characters;
providing access to one or more databases, the one or more databases including associations between a plurality of known words and a plurality of concepts, and including quantitative values representative of a strength of a relationship between the plurality of concepts;
identifying one or more of the plurality of groups of characters as corresponding to at least one of the plurality of known words;
creating a list of the identified known words;
querying the one or more databases to obtain a first set of semantic concepts associated with each of the identified known words;
annotating the list of identified known words with the first set of semantic concepts associated with each identified known word;
creating a semantic network having a plurality of nodes corresponding to the first set of semantic concepts;
iteratively expanding the semantic network with additional concepts taken from the one or more databases and linked to respective nodes in the semantic network to iteratively add new nodes to the semantic network for such additional concepts, each new node including a weighted link with an existing node, the additional concepts being separate from the first set of semantic concepts and including at least one episodic concept; and
selecting at least one of the concepts from the combination of the first set of concepts and the additional concepts based upon a value of the weighted link included with the node associated with the at least one selected concept.

18. The one or more non-transitory memory devices of claim 17, wherein the step of iteratively expanding will continue until a termination requirement is met.

19. The one or more non-transitory memory devices of claim 18, wherein the termination requirement is a value of a weighted link falling below a predefined threshold.

* * * * *